US007270691B2

(12) United States Patent
Arts et al.

(10) Patent No.: US 7,270,691 B2
(45) Date of Patent: Sep. 18, 2007

(54) INTEGRATED AIR PROCESSING DEVICES AND ISOLATION CONTAINMENT SYSTEMS USING SUCH DEVICES

(76) Inventors: Theodore A. M. Arts, 312 Countryside La., Williamsville, NY (US) 14221; Paul J. Chirayath, P.O. Box 5572, Key West, FL (US) 33040

( * ) Notice: Subject to any disclaimer, the term of this patent is extended or adjusted under 35 U.S.C. 154(b) by 0 days.

(21) Appl. No.: 11/089,795

(22) Filed: Mar. 25, 2005

(65) Prior Publication Data
US 2005/0211415 A1    Sep. 29, 2005

Related U.S. Application Data

(60) Provisional application No. 60/556,913, filed on Mar. 26, 2004.

(51) Int. Cl.
  F24C 15/20 (2006.01)
  F24F 7/00 (2006.01)
  A23C 3/02 (2006.01)
(52) U.S. Cl. .................. 55/385.2; 55/356; 55/473; 55/485; 55/DIG. 18; 55/DIG. 29; 55/DIG. 46; 454/158; 454/187; 600/21; 128/205.26; 165/59; 165/66; 96/224
(58) Field of Classification Search ........... 55/385.2, 55/356, 473, 485, DIG. 18, DIG. 29, DIG. 46; 454/158, 187; 600/21; 128/205.26; 165/59, 165/65, 66; 96/224
See application file for complete search history.

(56) References Cited

U.S. PATENT DOCUMENTS 4,071,080 A * 1/1978 Bridgers ............... 165/59

| 5,279,609 | A |  | 1/1994  | Meckler |
|---|---|---|---|---|
| 5,405,434 | A |  | 4/1995  | Inculet |
| 5,431,599 | A |  | 7/1995  | Genco |
| 5,664,995 | A |  | 9/1997  | O'Keefe |
| 5,916,096 | A |  | 6/1999  | Wiesmann et al. |
| 5,942,017 | A | * | 8/1999  | Van Winkle, Sr. ......... 55/385.1 |
| 5,976,010 | A |  | 11/1999 | Reese et al. |
| 6,126,540 | A |  | 10/2000 | Janu et al. |
| 6,245,132 | B1 |  | 6/2001  | Feldman et al. |

(Continued)

OTHER PUBLICATIONS

Koslow, Dr. Evan E., "Safegaurding America's HVAC Systems Against Chemical Warfare Threats", Filtration News, pp. 22, 24, 26, Jul./Aug. 2002, vol. 20—No. 4, Eagle Publications, Inc., Novi, Michigan.

Primary Examiner—Duane Smith
Assistant Examiner—Minh-Chau T. Pham
(74) Attorney, Agent, or Firm—Norris, McLaughlin & Marcus, P.A.

(57) ABSTRACT

In accordance with an embodiment of the invention, an integrated air processing device includes a housing defining an air inlet, an air outlet, and a pathway from the inlet to the outlet. An air decontamination section, an air conditioning section, and a heating section are provided along the pathway. A blower is also provided along the pathway, to drive air from the inlet to the outlet, along the pathway. In another example, an integrated air processing device includes a housing as above, and an air conditioning section and a heating section along the pathway. An air decontamination section and/or a blower may also be provided along the pathway. In accordance with another embodiment, a portable isolation containment system includes one or more portable containment enclosures coupled to the integrated air processing devices described above. Methods are disclosed, as well.

64 Claims, 19 Drawing Sheets

U.S. PATENT DOCUMENTS

| | | |
|---|---|---|
| 6,383,241 B1 | 5/2002 | Janus et al. |
| 6,402,613 B1 * | 6/2002 | Teagle ........................ 454/195 |
| 6,544,309 B1 * | 4/2003 | Hoefer et al. ................. 55/283 |
| 6,616,720 B1 * | 9/2003 | Smith ........................ 55/385.2 |
| 6,783,578 B2 * | 8/2004 | Tillman, Jr. .................. 96/224 |
| 6,796,896 B2 | 9/2004 | Laiti |
| 6,872,241 B2 | 3/2005 | Soane et al. |
| 6,966,937 B2 * | 11/2005 | Yachi et al. ................ 55/385.2 |
| 6,979,359 B2 * | 12/2005 | Laiti ........................... 55/356 |
| 2005/0145109 A1 * | 7/2005 | Dancey et al. ................ 95/273 |

* cited by examiner

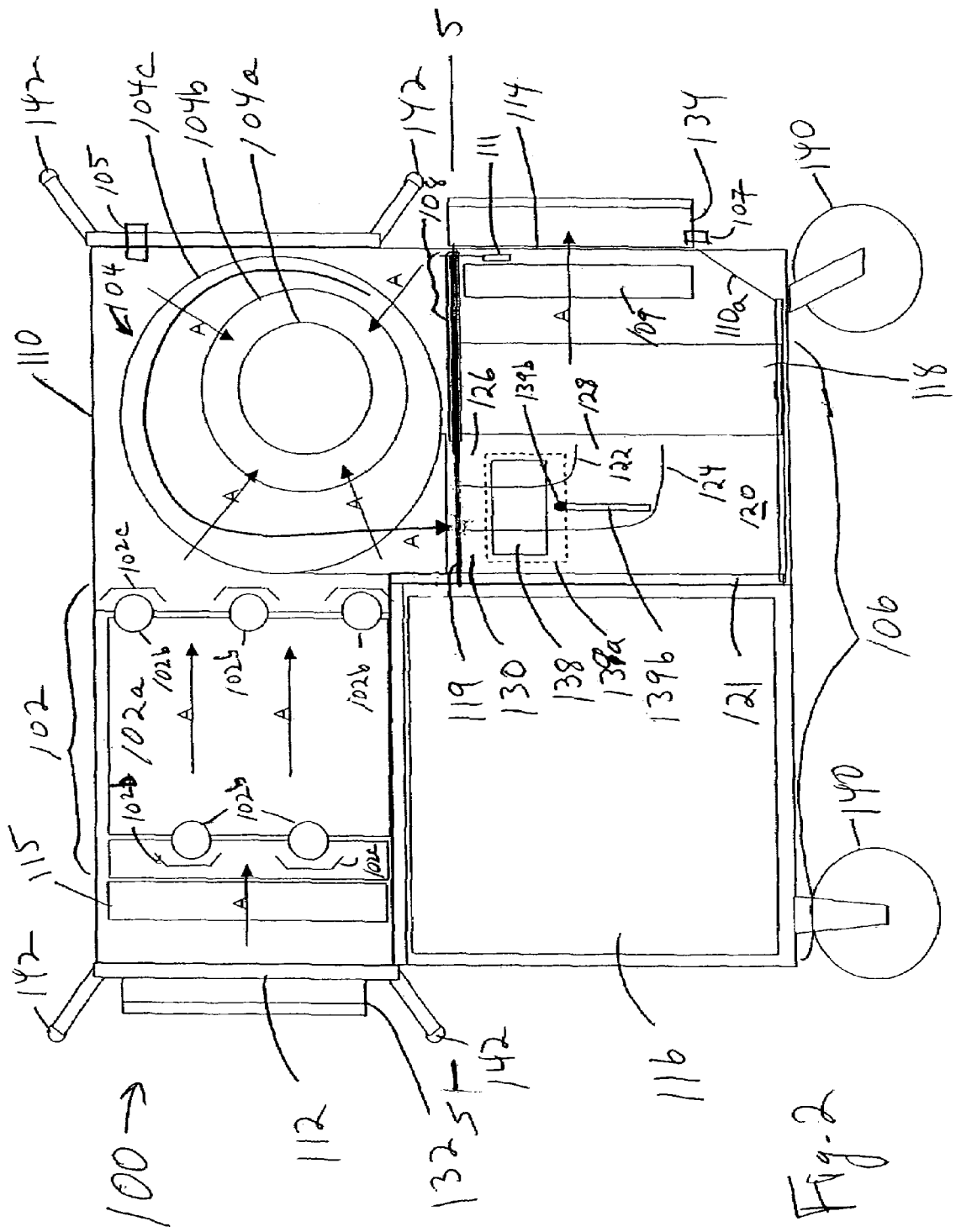

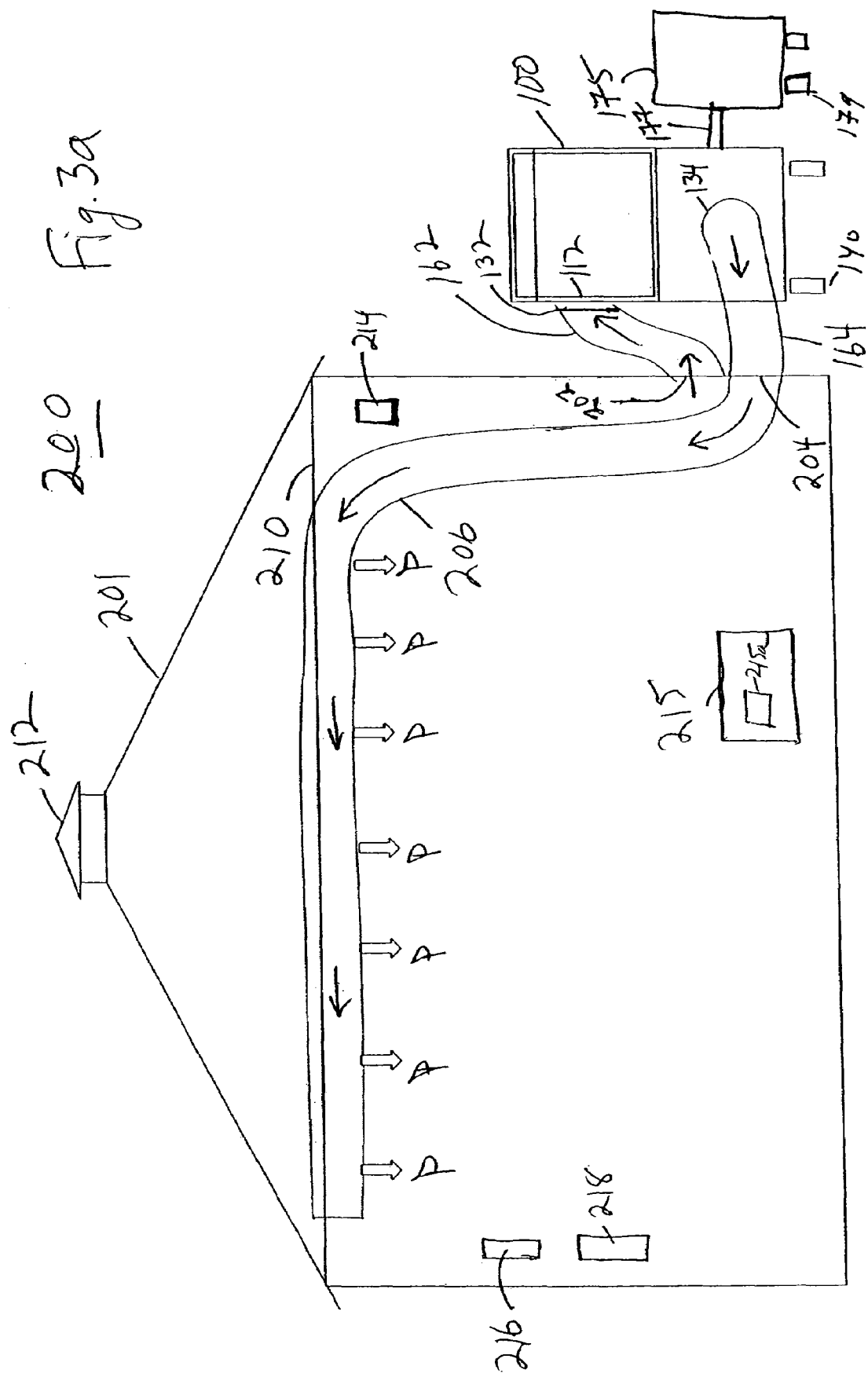

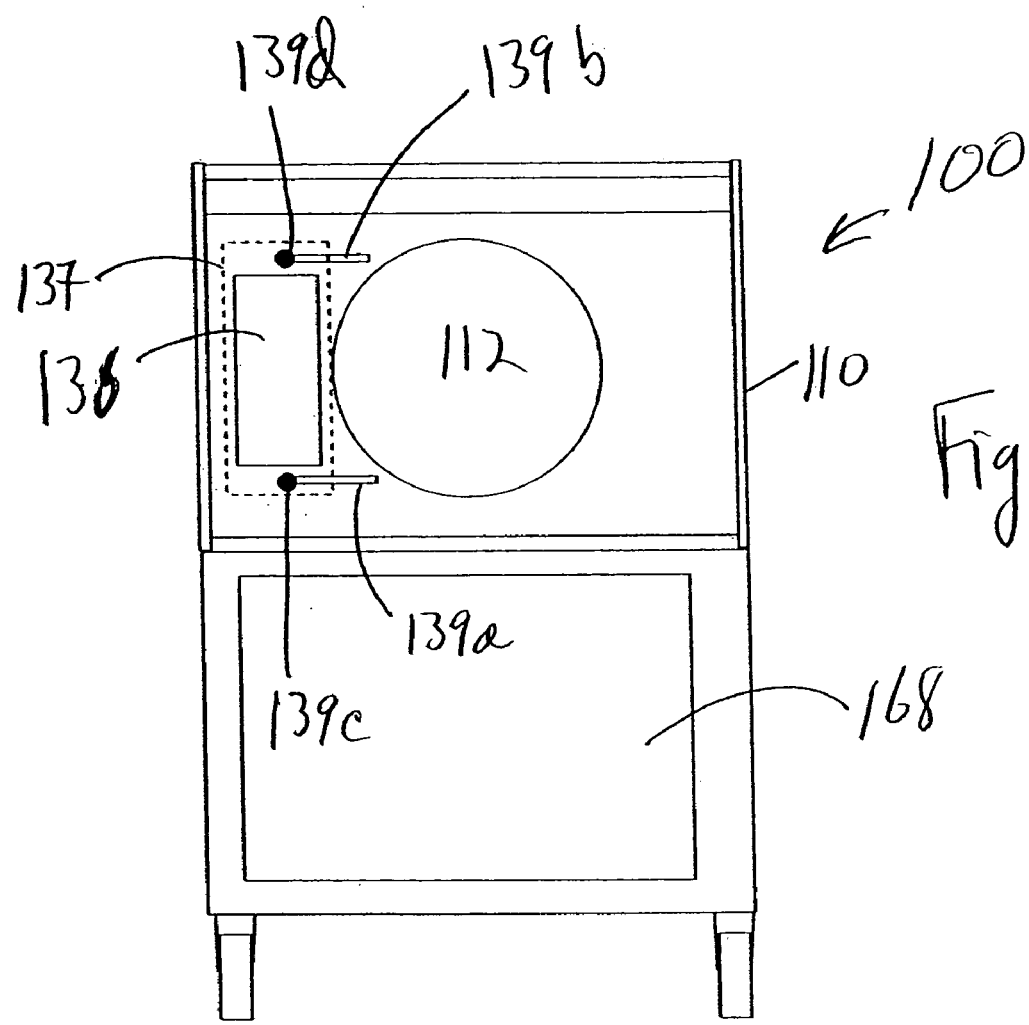

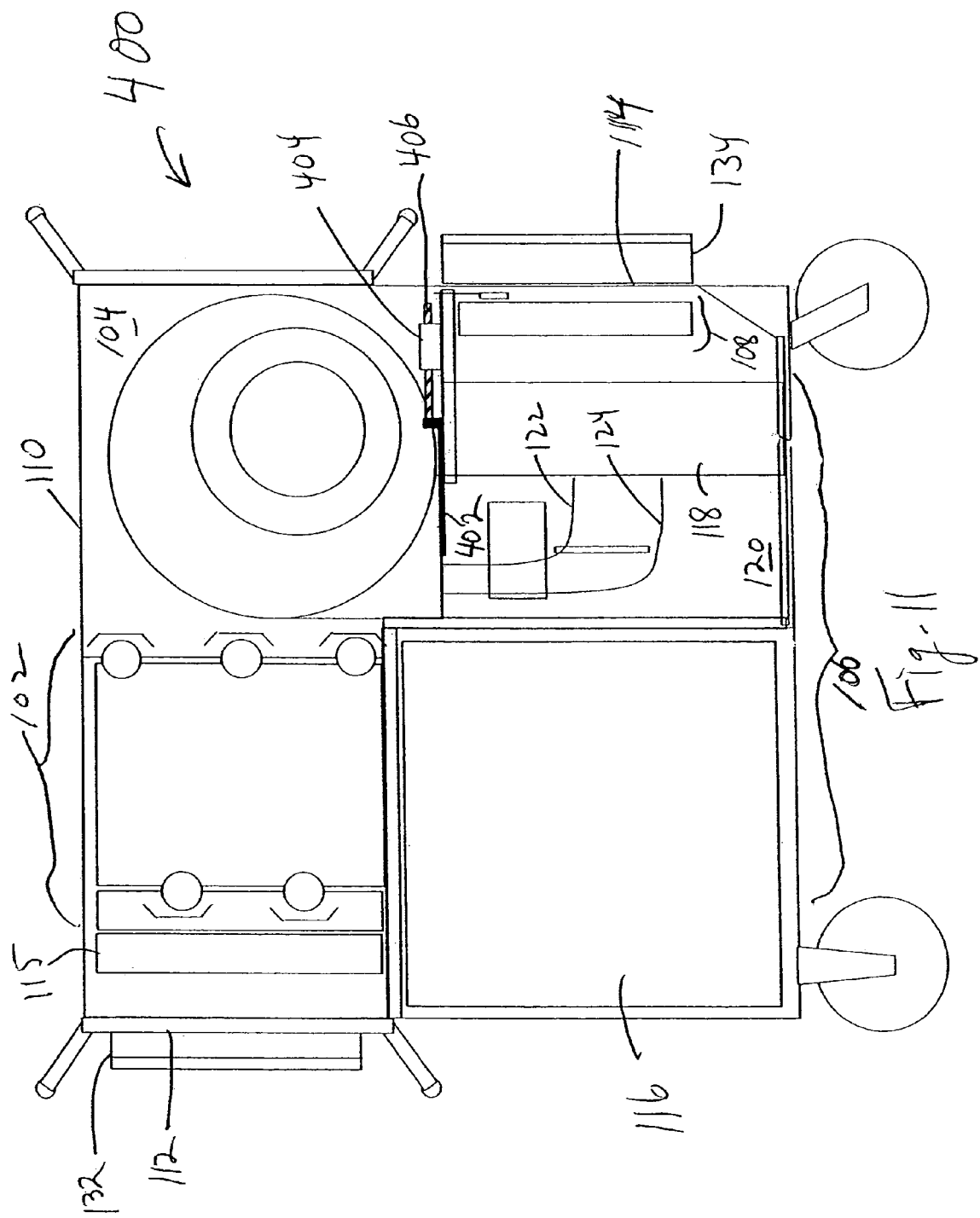

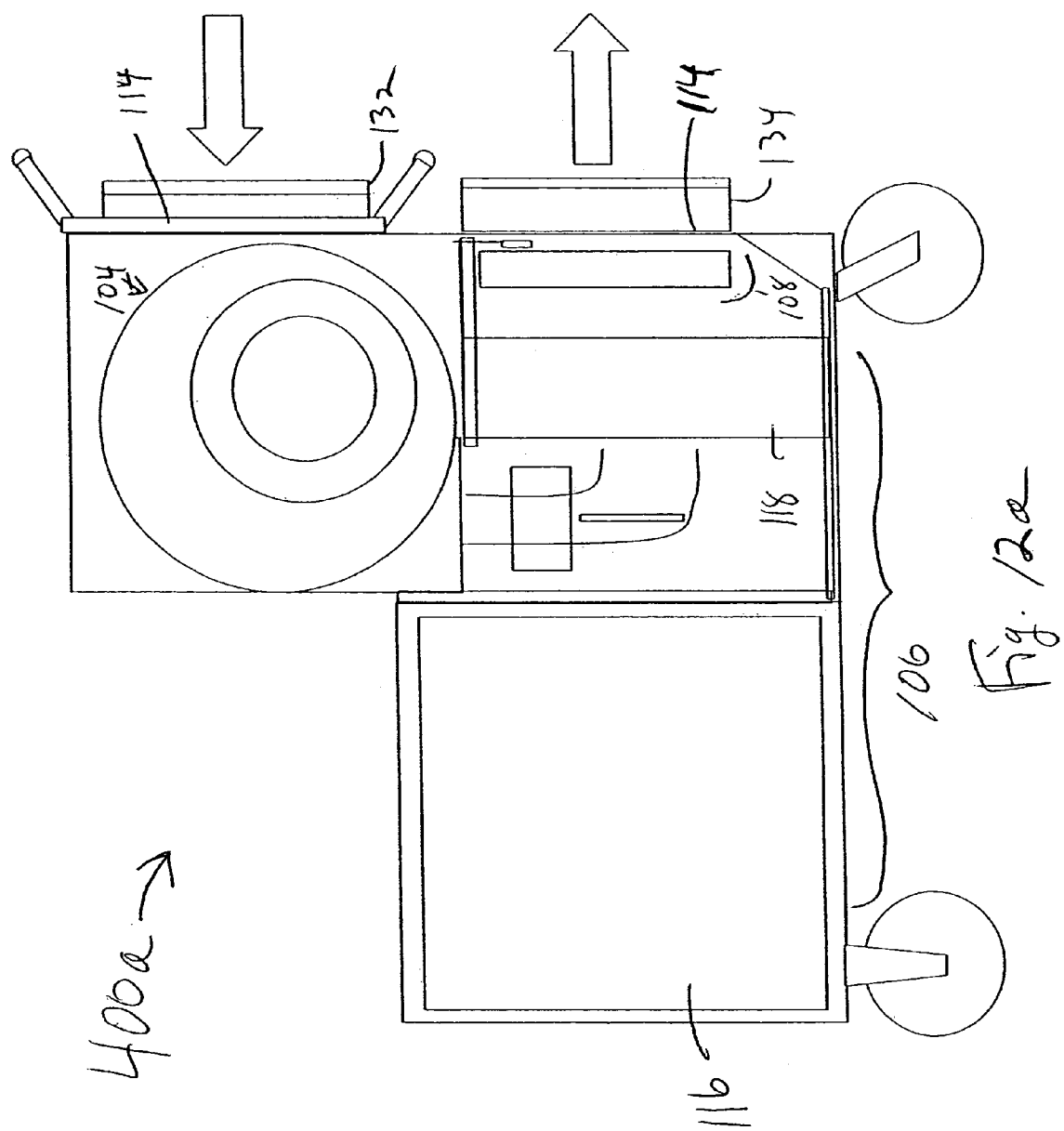

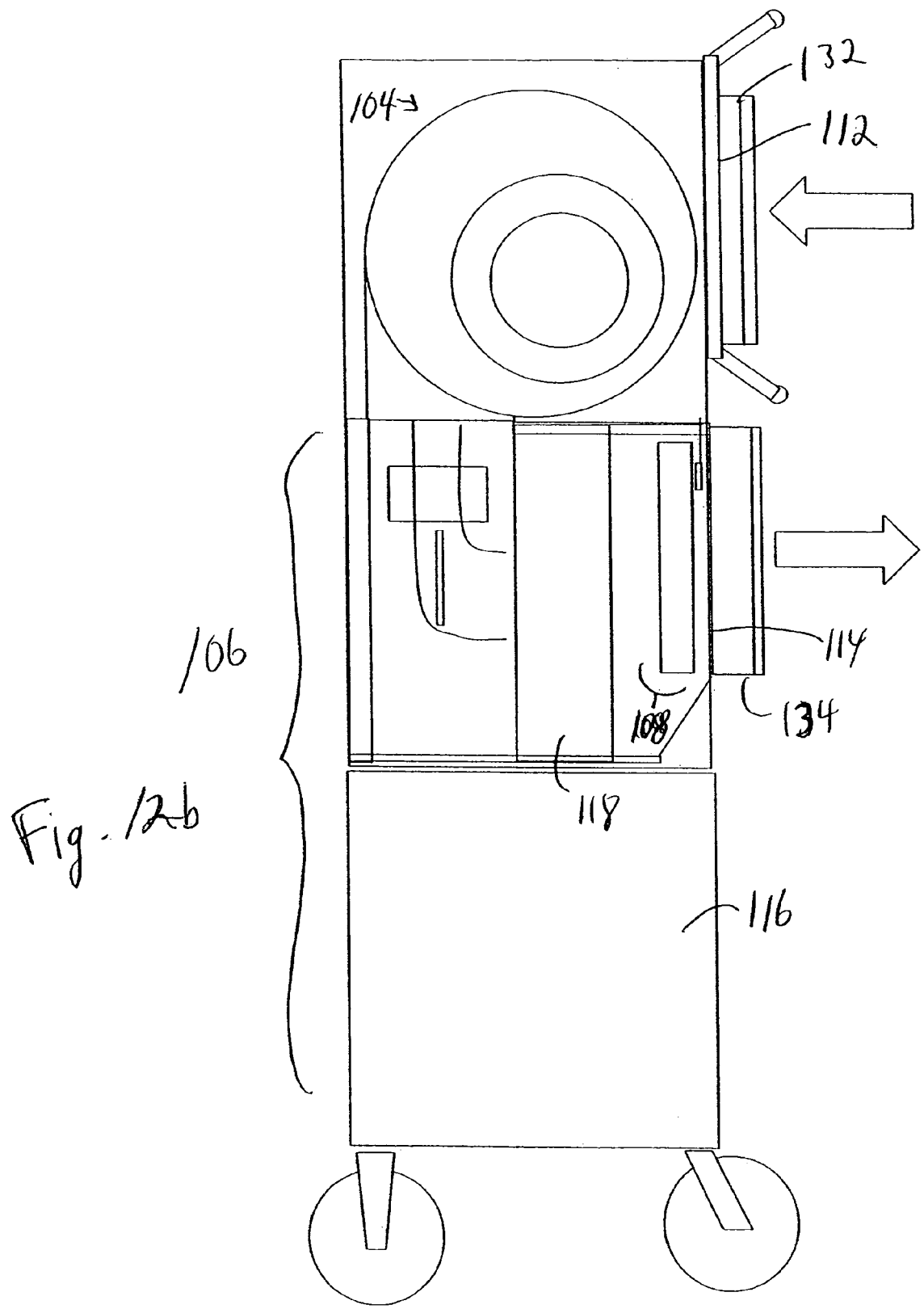

INTEGRATED AIR PROCESSING DEVICES AND ISOLATION CONTAINMENT SYSTEMS USING SUCH DEVICES

The present application claims the benefit of U.S. Application No. 60/556,913, filed on Mar. 26, 2004, which is incorporated by reference herein.

FIELD OF THE INVENTION

Integrated heating, ventilation, and air conditioning devices, integrated air decontamination, heating, ventilation, and air conditioning devices, and portable isolation containment systems ("PICS") using such devices.

BACKGROUND OF THE INVENTION

Tents are used by firefighting personnel near forest fires, to create command and control centers and to treat the wounded. If climate control is needed, portable air conditioning units and/or oil-based heating units are separately coupled to tents. Tents are also used to establish command and control and medical facilities by the military near battlefields.

It has also been proposed to use tents and other portable structures that may be quickly assembled in medical emergencies to house patients, as well as medical and command and control personnel. For example, hospital capacity may need to be increased to handle patients from a large accident, an epidemic, or a natural disaster. Portable medical facilities may also need to be quickly assembled at or near a site of a medical emergency, such as a fire, or a chemical, biological, or a nuclear accident or incident, such as a terrorist attack.

Temperatures may vary widely across regions and in the same location during different times of the year and different times of the day. Temperature variations over 80% of the United States and other temperate regions lie within the range of from about 0° F. (−18° C.) to about 100° F. (38° C.). Typical temperature variations over climate extremes from the arctic to the desert lie within the range of from about −20° F. (−11° C.) to about 120° F. (48° C.). The temperature variation in a single location may vary from 100° F. (38° C.) in the summer to 0° F. (−18° C.) in the winter. The temperature variation in a location may also vary from 80° F. (27° C.) during the day to 50° F. (18° C.) at night, for example, at certain times of the year. Cooling may therefore be required during the day while heating is required at night.

An optimum temperature range for comfort is between about 68° F. and 72° F. (about 20° C. and 22° C.), for example. Since the optimum temperature range is closer to the upper end of the above temperature ranges than to the lower end, cooling is required over a smaller portion of the ranges than heating. In the summer, for example, cooling could be required for up to about 30 Fahrenheit degrees (17 centigrade degrees) (from 100° F. (38° C.) to 70° F. (21° C.), for example) in a temperate climate. In the winter, in contrast, heating may be required up to about 70 Fahrenheit degrees (39 Centigrade degrees) (from 0° F. (−18° C.) to 70° F. (21° C.), for example). Heating a tent in certain locations may therefore require about twice as many BTUs of heat as BTUs of cooling to cool the tent.

Air conditioning units typically comprise an evaporator, a condenser, and a compressor. Refrigerant fluid for cooling flows through coils in the evaporator. A fan moves air to be cooled through the evaporator, over the coils. The fluid absorbs heat from the air, which cools the air and vaporizes the refrigerant fluid. The vaporized fluid is pumped to the condensor by the compressor. In the condensor, which also comprises coils, the vapor condenses, releasing the heat to air or other such medium flowing through the condensor, removing the heat from the unit. The refrigerant is then pumped back to the evaporator.

FIGS. 1a-1c are schematic representations of three types of standard evaporators: 1) an up flow V-shaped evaporator 10; 2) a horizontal flow evaporator 20; and 3) a window-type evaporator 30. The evaporators comprise coils 50. Due to their low temperature, moisture 40 condenses on the evaporator coils 50. The moisture is forced off of the coils 12 by the air flow F and drips or runs down the outside of the evaporator into drip pans 60, due to the force of gravity. The V-shaped evaporator 10 and the horizontal flow evaporator 20 are angled with respect to the air flow F, to facilitate drainage. The face of the window-type evaporator 30 is normal to the air flow F. Air flow F through these evaporators 10, 20, 30 is uniform across the face of the evaporator, and across the coils 50.

SUMMARY OF THE INVENTION

An air conditioner can only efficiently process a certain air flow (feet per minute (meter per minute) or cubic feet per minute ("CFM") (cubic meter per minute ("CMM")), for example). As mentioned above, for a single device to provide cooling and heating over the temperature ranges for temperate climates (0° F. (−18° C.) to 100° F. (38° C.)) or extreme climates (−20° F. (−11° C.) to 120° F. (48° C.)), the device must generate almost twice as many BTUs of heating than BTUs of cooling, in a single location. The wattage of the heating coils or lamps required to generate the required number of BTUs of heating require higher air flow rates to prevent overheating of the heating elements than the optimum air flow for efficient cooling. In addition, higher air flow is required to reach an optimum temperature range from very low initial temperatures and to maintain the optimum range in a cold environment. In one example, 68,000 BTUs (17,000 kilocalories ("kcal") of heating may be required while only 36,000 BTUs (9,100 kcal) of cooling may be required in the same location. It is therefore difficult for a single air processing unit to provide both heating and cooling over the wide temperature ranges that may be found across regions throughout the year and even in the course of a day, when cooling may be required during the day and heating at night.

Air conditioning and heating devices used in hostile environments, such as near fires, tend to become contaminated. The use of air conditioning and heating devices with facilities housing contagious patients can result in biological contamination by bacteria and/or viruses. Similarly, if used at the site of a chemical, biological, or nuclear accident or incident, serious contamination would result. Decontaminating and certifying such devices is expensive. Contaminated devices are therefore often discarded. In the case of biological, chemical, and nuclear contamination, even proper disposal is difficult and expensive as only certain facilities can accept hazardous wastes.

A single device that can provide heating and cooling over broad temperature ranges would be advantageous. A single device that can provide heating, cooling, and air decontamination would also be advantageous.

In accordance with an embodiment of the invention, an integral air processing device is disclosed comprising a housing defining an air inlet, an air outlet, and a pathway from the inlet to the outlet. An air decontamination section, an air conditioning section, a heating section, and a blower are provided along the pathway, to drive air from the inlet to the outlet, along the pathway. The housing may further define an inlet vent upstream of the blower and separate from the air inlet, to allow for the entry of air to the pathway. The housing may further define an outlet vent downstream of the blower and separate from the air outlet, to allow for the exit of air from the pathway. The entry of air through the inlet vent or the exit of air through the outlet vent enables the creation of positive or negative pressures in a structure ventilated by the air processing device, respectively. The air conditioning section may also operate as a heat pump.

The air conditioning section may comprise an evaporator along the pathway. Means may be provided to slow the airflow through the evaporator when the air conditioning section is activated. For example, more air may be provided to a bottom portion of the evaporator than to an upper portion. This is believed to "load" the lower portion with air and "load' the upper portion with moisture, slowing the airflow through the evaporator. The evaporator may also be positioned transverse to the airflow. A damper may also be provided to move over the pathway to decrease airflow to the evaporator when the air conditioning section is on. The blower speed may also be decreased when the air conditioning section is on. Reducing the air flow when the air conditioning section is on facilitates efficient operation. Higher airflow may then be used when the air conditioning section is not on, which is desirable for operation of the heating section.

The evaporator has an downstream side having a surface area that is preferably greater than the surface area of the entrance to the outlet of the device. The heating section may comprise at least one heating element occupying an area about the same as the area of the entrance to the outlet.

A processor may be coupled to the device. The processor may be configured to, at least in part, monitor operation of the device and/or control operation of the device.

In accordance with a related embodiment, an integral air processing device is disclosed comprising a housing defining an air inlet, an air outlet, and a pathway from the inlet to the outlet. The device further comprises an air conditioning section and a heating section along the pathway. A blower may be provided within the device to drive air from the inlet to the outlet, along the pathway.

In accordance with another embodiment of the invention, a portable isolation system is disclosed comprising a portable containment enclosure defining an interior to house subjects, for example. The subjects may be medical patients, medical professionals and/or control personnel, for example. The system also comprises an integrated air processing device to provide air conditioning and heating. The air processing device is coupled to the portable containment enclosure to process air within the enclosure to provide heating, ventilation and/or air conditioning to the enclosure during operation. The integrated air processing device may have any or all of the features discussed above, including air decontamination.

At least one second portable containment enclosure may be coupled to the first enclosure. Personnel may move between the enclosures. At least one respective second integrated air processing device is coupled to the second enclosure, to provide heating, ventilation and/or air conditioning to the at least one second portable containment enclosure, during operation. A chamber may be provided between the first portable containment enclosure and the at least one second portable containment enclosure, to decrease air flow and possible contamination between the enclosures. The portable containment enclosure may be a tent, for example. Air decontamination may be provided in either or both of the integrated air processing devices, as well.

In accordance with another embodiment of the invention, a method of processing air by a device disclosed. The device comprises an air conditioning section, a heating section, and a pathway extending from an inlet of the device, through the air conditioning and heating sections, to an outlet of the device. The method comprises receiving air through the inlet to the device. The method further comprises cooling a first air flow passing through the air conditioning section, when the air conditioning section is on, and heating a second air flow passing through the heating section, when the heating section is on. The second air flow is greater than the first air flow. Air is driven out of the device, though the outlet. The method may further comprise decreasing the air flow through at least the air conditioning section from the second air flow to the first air flow, when the air conditioning section is on. The method may further comprise decontaminating air received from a portable containment enclosure.

In accordance with another embodiment, a portable isolation system is disclosed comprising a portable containment enclosure and an air decontamination device coupled to the enclosure to decontaminate air within the enclosure.

BRIEF DESCRIPTION OF THE FIGURES

FIG. 2 is a side schematic view of an interior of an example of an air decontamination, heating, ventilation, and air conditioning device ("ADHVAC'), in accordance with an embodiment of the invention.

FIG. 3a is a schematic diagram of an example of a portable isolation containment system ("PICS") in accordance with an embodiment of the invention, comprising the ADHVAC of FIG. 2 connected to a portable isolation enclosure ("PIE"), such as a tent;

FIG. 3b is a side view of an example of the air sampling manifold shown in FIG. 3a;

FIG. 7a and FIG. 7b are front views of an ADHVAC of FIG. 2, showing the inlet and an intake portioning vent;

FIG. 11 is a schematic diagram of an ADHVAC including a sliding damper to control air flow to the evaporator, in accordance an embodiment of the invention;

FIGS. 12a and 12b are examples of integrated heating ventilation and air conditioning devices ("IHVAC"), in accordance with an embodiment of the invention;

FIG. 13b is a front perspective view of a filter for use in the air decontamination section of FIG. 13a.

DETAILED DESCRIPTION OF THE PREFERRED EMBODIMENTS

Figure 1A:
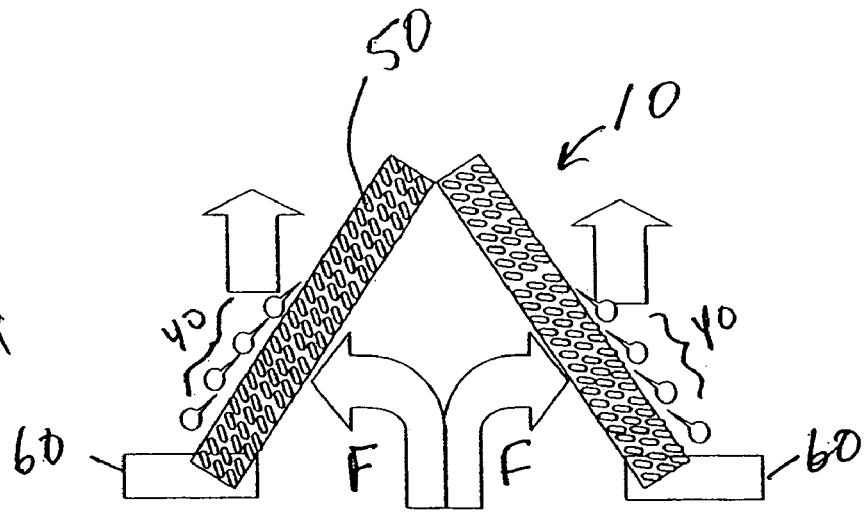
FIGS. 1a-1c are schematic representations of three types of standard evaporators.
Figure 1B:
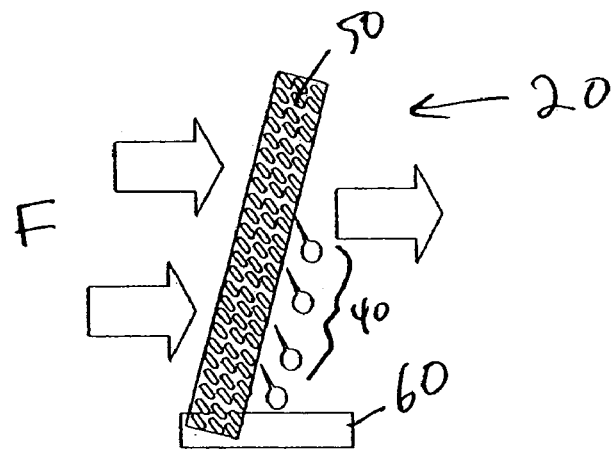

In one embodiment of the invention, an integrated air processing device comprises air decontamination, heating, and air conditioning sections to provide air decontamination, heating, ventilation, and cooling, within a single body. Such a device is referred to herein as an "ADHVAC." In another embodiment, an integrated air processing device comprises heating and cooling sections, also within a single body. Such a device is referred to as an "IHVAC." The body in each case may comprise a housing having one or more integrated housing sections. As discussed above, in the ventilation of portable structures, heating, air conditioning and air decontamination are typically provided by separate units and air decontamination is typically not provided.

In another embodiment of the invention, a portable isolation containment system ("PICS") comprises a portable isolation enclosure ("PIE"), such as a tent, and an ADHVAC or IHVAC device coupled to the PIE. The ADHVAC or IHVAC may be inside of or outside of the PIE. The PICS, which may be quickly assembled, is particularly useful in emergency situations requiring a rapid ability to accommodate an unexpected number of patients, such as in an outbreak or epidemic of an infectious disease, an industrial accident, a fire, a biological, chemical or nuclear accident or incident, a terrorist attack, and a natural disaster, for example. The ADHVAC and IHVAC provide climate control of the PIE. By combining heating and air conditioning, and optionally air decontamination, into one integrated device, in accordance with embodiments of the invention, the PICS requires fewer components, is easier to deploy, and is easier to store than the options provided in the prior art. Unless air decontamination is being discussed, references to ADHVAC includes the IHVAC; as well.

FIG. 2 is a side schematic view of an interior of an example of an ADHVAC 100 in accordance with an embodiment of the invention, which may be used in a PICS or in other applications. The ADHVAC 100 in this example comprises an air decontamination section 102, a blower 104, an air conditioning ("AC") section 106, and a heating section 108, contained within a housing 110 to form an integrated unit. The housing 110 has an inlet 112 and an outlet 114, which are typically circular but can be any shape. The housing 10 may comprise multiple housing sections assembled to form a single integrated body that is also referred to herein as the housing 110. Arrows "A" indicate air flow along a pathway from the inlet 114 to the outlet 116. While it is preferred that the AC section 106 be upstream of the heating section 108, that is not required.

The blower 104 in FIG. 2 is a schematic representation of a motor 104a, a fan 104b, and a housing 104c, as is known in the art. In the configuration of FIG. 2, the blower rotates counterclockwise. The blower 104 is preferably downstream of the air decontamination section 102 and upstream of the AC section 106 and the heating section 108, so that contaminated air is decontaminated before passing through the AC and heating sections. As a result, only decontaminated, clean air passes through the blower 104, AC section 106, and heating section 108, protecting these sections from contamination. This prolongs the life span of these sections and reduces cleaning requirements. While preferred, this configuration is not required. A port 105 may be provided through the housing 110, proximate the blower 104, for connection to an air sampling manifold, as discussed further below. The port 105 should be upstream of the blower 104, so that air is drawn into the ADHVAC 100. The blower may be a multi-speed blower, so that the ADHVAC 100 may be used with portable isolation enclosures ("PIEs") of different sizes. The blower 104 may also be a single speed blower. The blower 104 is preferably provided within the ADHVAC 100, although that is not required. The blower may also be a separate unit coupled to the inlet 112 or the outlet 114 to blow or draw air through the ADVAC 100. A single speed blower may be obtained from W. W. Grainger, Inc., Buffalo, N.Y., for example. Model Number 4C831, which is rated at 1,500 CFM (42 CMM) in free air, may be used, for example.

The air decontamination section 102 is preferably able to capture, contain, and neutralize biological agents in the air, such as viruses, bacteria, and spores, and to remove airborne particles from the air, such as soot and smoke. The air decontamination section 102 may comprise a filter 102a, such as a HEPA filter. A preferred filter arrangement further comprises an ultraviolet ("UV") lamps 102b upstream and downstream of the filter 102a and reflectors 102c positioned to reflect light directed away from the filter, towards the filter. The filter 102a may be a V-bank HEPA filter and the UV lamps may be positioned within regions defined by the V's, as shown and described in U.S. application Ser. No. 10/434,041 ("the '041 application"), which was filed on May 8, 2003, and PCT publication WO 2004/011041 A2 ("the '1041 publication"), which was published on Feb. 5, 2004. The '041 application and the '1041 publication are assigned to assignee of the present invention and are incorporated by reference herein. A preferred air decontamination system 102 is described further below, with respect to FIGS. 13a and 13b. It is noted that other types of filters may be used, as well.

A prefilter 115 may also be provided upstream of the decontamination section 102, to remove larger particles of dirt and dust, for example, prolonging the life of the HEPA filter 102a. The prefilter 115 may be fixed within the housing 110 downstream of the air inlet 112 and upstream of the air decontamination section 102, for example. The choice of prefilter 115 may depend upon the expected type(s) of contaminants in the air. The housing 110 preferably includes a door (not shown) to allow access to the prefilter 115, enabling the prefilter to be changed if a different prefilter is desired or if the prefilter is contaminated. Prefilters may also remove gases. A prefilter 115 is not typically used in biological events because decontamination and/or disposal of a prefilter contaminated with biological agents, may be difficult. In one example, the prefilter 115 may be an activated carbon sprayed on filter, which has a large surface area and tiny pores that capture and retain gases and odors. Activated carbon filters are readily commercially available. Prefilters are discussed further in the '041 application and the '1041 publication, which are incorporated by reference herein.

Figure 5:
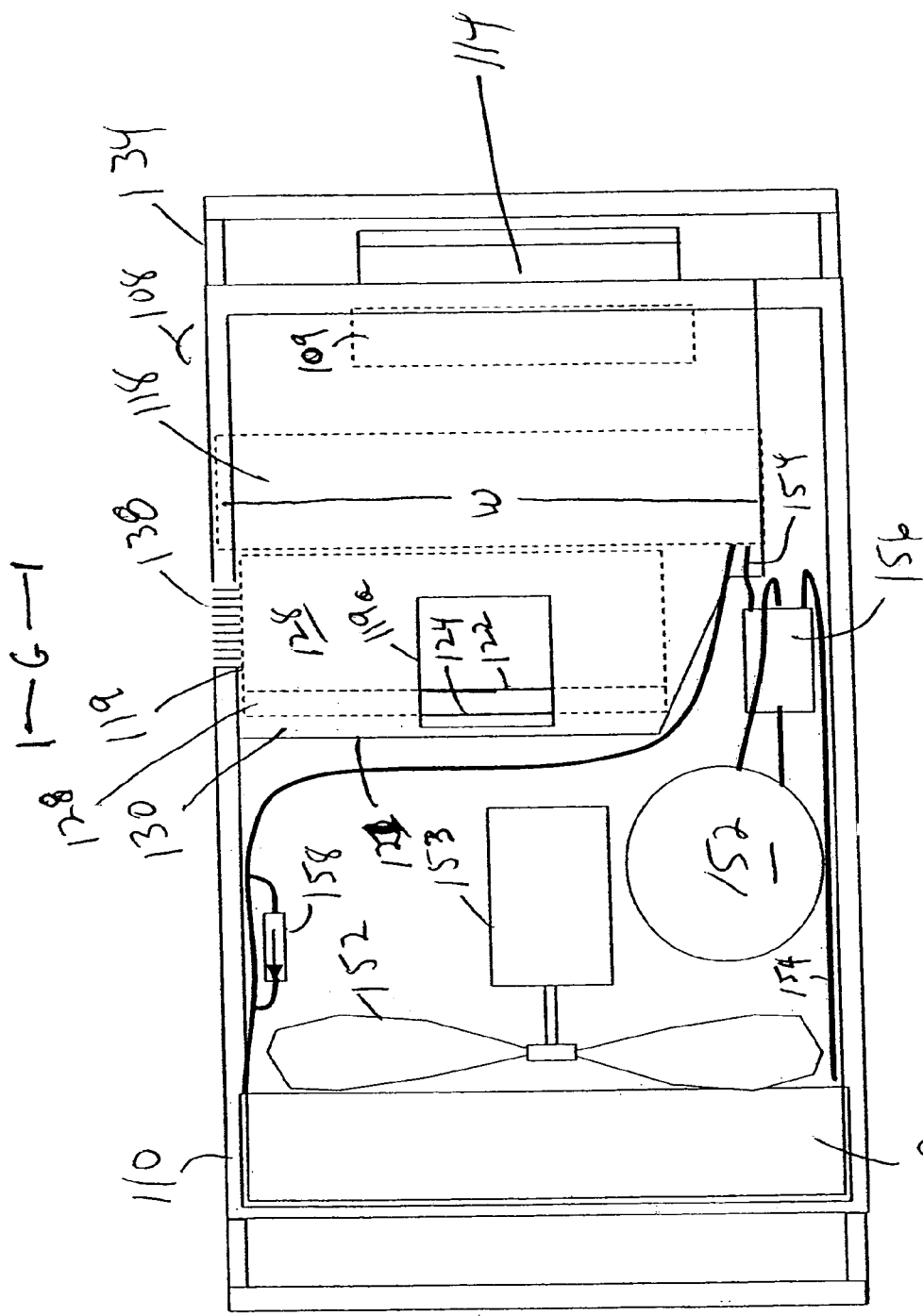
FIG. 5 is a top view of the lower portion of the ADHVAC of FIG. 2, with the upper portion removed, along line 5-5 of FIG. 2.

The AC section 106 comprises a condenser section 116 and an evaporator 118, as is known in the art. The evaporator 118 is preferably positioned vertically, to minimize the size of the ADHVAC 100, but that is not required, as discussed further below. An interior wall 121 is provided between the condenser section 116 and the evaporator 118. A plate 119 is provided between the blower 104 and the AC section 106, with a passage 119a (shown in FIG. 5) for air to pass from the blower 104 into the AC section 106. A gap 120 is provided between the interior wall 121 and the evaporator 118 to accommodate air flow A from the blower 104, through the passage 119a. In this example, two baffles 122, 124 are provided in the gap 120 to define three channels 126, 128, 130 along the pathway to guide the air flow A towards the evaporator 118. Preferably, the baffles 122, 124 terminate close to the evaporator 118, such as within about 1 inch (25 mm) of the evaporator. The separation between the baffles 122, 124 is exaggerated in FIG. 2, for ease of illustration. FIG. 5 shows the positions of the baffles 122, 124 more accurately. The components of the condenser section 116 are discussed further below with respect to FIG. 5. The AC section 106 may comprise commercially available, off the shelf components.

The heating section 108 comprises one or more heating elements 109, such as electrical heating coils or lamps. The heating elements 109 are preferably proximate the outlet 114. One or more temperature sensors 111 are preferably provided to monitor the temperature of the heating elements 109.

An intake duct attachment collar 132 may be coupled to the ADHVAC 100 at the inlet 112. An outlet duct attachment collar 134 may be coupled to the ADHVAC 100 at the outlet 114. Ducting, shown in FIG. 3a, for example, may be connected to the collars 132, 134 to provide air flow of the ADHVAC 100 and a portable isolation enclosure (PIE) such as a tent, or other such structure. A port 107 may be provided through the outlet duct collar 134, or in another location downstream of the blower 104, so that air may be drawn from the pathway, to enable sampling of the air processed by the ADHVAC 100, as discussed further below.

An outlet vent 138 is provided in the gap 120 to allow for the escape of air A from the pathway, to enable creation of a negative pressure within the PIE, as discussed further below. A sliding damper 139a, which moves within a guide slot 139b, is provided on an interior wall of the housing 110, to open and close the vent 138.

The ADHVAC 100 also comprises wheels 140 and handles 142 to facilitate deployment of the device 100.

FIG. 3a is a schematic diagram of an example of a portable isolation containment system ("PICS") 200 in accordance with an embodiment of the invention, comprising an ADHVAC 100 connected to a portable isolation enclosure ("PIE") 201, such as a tent. An electrical generator 175 is shown electrically coupled to the ADHVAC 100 via an electrical cable 177. The generator may have wheels 179, as well. The inlet 112 of the ADHVAC 100 may be coupled to the interior of the PIE 201 via inlet ducting 162 coupled to the intake duct attachment collar 132 and to an outlet opening 202 of the PIE 201. The outlet 114 may be coupled to the interior of the PIE 201 via outlet ducting 164 coupled to the outlet duct attachment collar 134 and to an inlet opening 204 of the PIE. The inlet opening 204 of the PIE 201 in this example is coupled to interior ducting 206 that extends to and across one or more upper portions 210. Openings in the ducting 206 allow for the exit of processed air into the interior of the PIE 201, as indicated by arrow "P". This is has been found to provide even distribution of the processed air throughout the PIE 201. Commercially available quick release ducting may be used, to facilitate assembly and disassembly of the PIE 201.

One or more vents 212 are provided to allow for venting into or out of the PIE 201, as necessary, as discussed below. The ADHVAC 100 may be positioned within the PIE 201, as well, in which case the ducting may or may not be provided. If positioned inside the PIE 201, ducting is preferably provided to convey air passing through the condenser 116 out of the PIE. Ducting would also be provided from the outlet vent 138 out of the PIE, as well as from an inlet vent 136 provided to enable creation of a positive pressure in the PIE (See FIG. 7a), out of the PIE.

A remote thermostat 214 may be provided in the PIE 201. Operation of the AC section 106 and the heating section 108 may be based on the thermostat via a switch or a processor, such as a microprocessor 215. The thermostat 214 may be a commercially available thermostat, programmable for temperature and time, for example. Instead of controlling the AC section 106 and the heating section 108 by the microprocessor 215 or switch, a dual rate thermostat, that allows for variable control of the heating elements 109, may be used. For example, with dual rate thermostat, a first heating element may be turned on when the detected temperature drops below a temperature threshold. If the temperature does not rise above the threshold within a predetermined period of time, then another heating element may be activated. A Model 1F81 dual rate thermostat available from White Rogers, Incorporated, St Louis, Mo., may be used, for example.

Figure 3B:
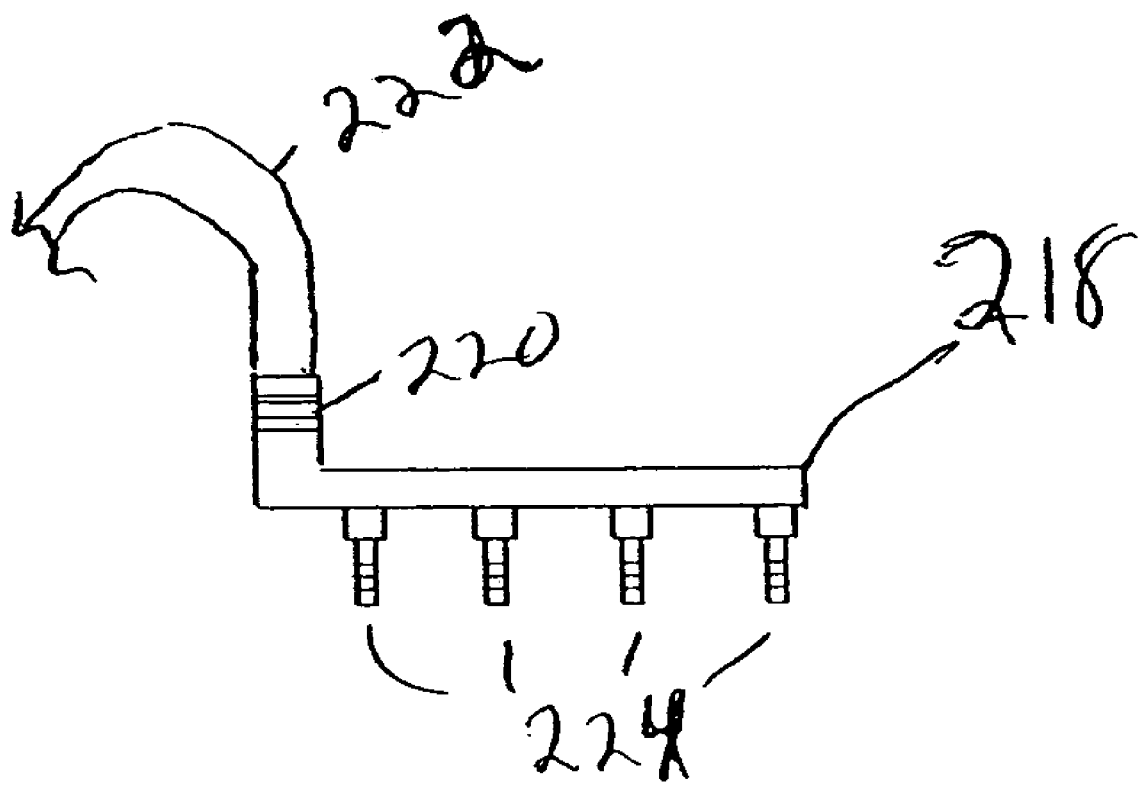

An air sampling manifold 218 may also be provided within the PIE 201, suspended from the ceiling or a wall, for example, to enable air sampling of the air in the PIE, as well as the air processed by the ADHVAC 100. FIG. 3b is a side view of an example of the air sampling manifold 218 shown in FIG. 3a. The manifold 218 has a first end 220 that may be coupled to the port 105 of the ADHVAC 100 (see FIG. 3b) via tubing 222. Air sampling nipples 224 are provided for connection to air sampling tubes and/or particulate collectors (not shown), as are known in the art and are described in the '041 application and the '1041 publication, which are incorporated by reference herein. Air is drawn through the tubing 222, the manifold 218, the nipples 224, and the sampling tubes and/or particulate collectors, by the blower 104. The air collected in the sampling tubes/particulate collectors may be analyzed, as is known in the art and as described in the '041 application and the '1041 publication, to identify contaminants in the air. Air sampling tubes and particulate collectors may also use color change, for an immediate indication or identification of a contaminant. For example, sorbent tubes may be used to identify the presence of carbon monoxide or chlorine. Air processed by the ADHVAC 100 may also be sampled by connecting one or more sampling tubes/particulate collectors by tubes to the port 107 downstream of the blower 104 (see FIG. 2), to evaluate the operation of the ADHVAC. Processed air exiting the ADHVAC 100 is then drawn by the blower 104 through the tubes, the sampling tubes/particulate collectors, the nipples 224, the sampling manifold 218, the tube 222, and the port 105.

Figure 3C:
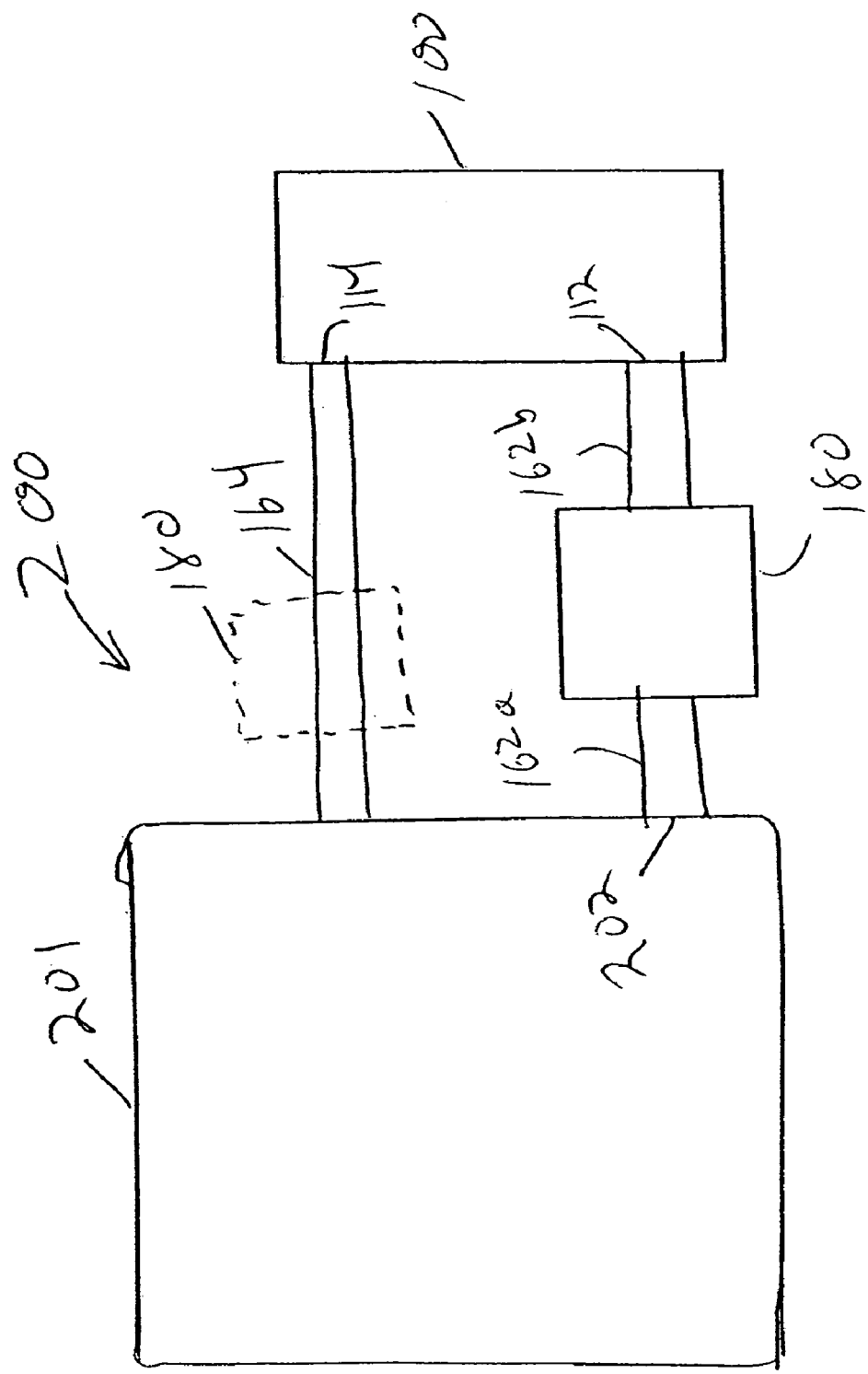
FIG. 3c is a schematic view of the ADHVAC of FIG. 2 coupled to the PIE of FIG. 3, through a high efficiency gas absorber (HEGA) unit.

A high efficiency gas absorber ("HEGA") unit 180 may be coupled between the inlet 112 of the ADHVAC 100 and the outlet 202 of the PIE 201, to provide filtration of chemical or nuclear contaminants, as shown schematically in FIG. 3c. Ducting 162a and 162b may be provided. HEGA units are known in the art and are described in more detail the '041 application and the '1041 publication, which are incorporated by reference herein. The HEGA unit 180 may be coupled between the outlet 114 of the ADHVAC 100 and the PIE 201, as shown in phantom, instead of between the outlet 112 and the PIE 201. Appropriate HEGA units are available from R. P. Fedder Corporation, Rochester, N.Y., for example.

Referring to FIGS. 2 and 3a, during operation, the blower 104 of the ADHVAC 100 draws air from the PIE 201 into the inlet 112, through the outlet 202 and the inlet ducting 162. The air is drawn through the prefilter 115, if present, and through the air decontamination section 102. The decontaminated air is then blown into the gap 120 between the condensor 116 and evaporator 118, and through the evaporator. The air continues through the heating section 108 and out of the unit through the outlet 114. Either the AC section 106 or the heating section 108 may be "on" to cool or heat the decontaminated air, respectively, as needed. Neither may be on, as well. The processed air is returned to the PIE 201 via the outlet ducting 164 and the PIE outlet 204.

In one example, the PIE 201 may be a tent that is about 19 feet wide (5.8 m), 35 feet long (10.7 m), and 11 feet high (3.4 m), and a volume of about 4,000 cubic feet (113 cubic meters). The blower 104 moves about 1,500 CFM (42 CMM) of air. With an air decontamination section 102 as described herein, the air within the tent 201 may be completely decontaminated in 12 passes through the ADHVAC 100, or less, depending on the contaminant. For example, while biological and chemical contamination typically require 12 passes, soot and smoke may be cleared in 4 passes. The ADHVAC 100 can perform 12 air exchanges of the PIE 201 in 1 hour.

Also in this example, the ADHVAC 100 is operable over a temperature range of 0° F. (−18° C.) to 100° F. (38° C.). In order for the AC section 106 to cool the tent 201 across this temperature range, it must have a rating of 36,000 BTUs (9,100 kcal), which requires an air flow of from about 800 CFM (23 CMM) to about 850 CFM (24 CMM), for efficient operation. In order for the heating section 108 to heat a tent of this size across this temperature range, the heating elements 109 need to have a rating of 68,000 BTUs (17,000 kcal). In this example, the air flow required to generate 68,000 BTUs (17,000 Kcal) without overheating the heating elements, and to be distributed through the tent for effective heating, is at least about 1,100 CFM (31 CMM).

As mentioned above, the blower 104 moves about 1,500 CFM (42 CMM) of air. The air decontamination section 102 in this example includes a HEPA filter that is 11.5 inches (29.2 cm) thick, which decreases air flow by about 400 CFM (11 CMM). About 1,100 CFM (31 CMM) is therefore pushed toward the AC section 106 and the heating section 108. Since only about 800 CFM (23 CMM) to 850 CFM (24 CMM) should be moved through the AC section 106 for efficient operation but as much air flow as possible is desired through the heating section 108 to prevent overheating, a mechanism is needed to decrease the airflow through the AC section 106 when the AC section is on, but allow higher air flow when the AC section is off and/or when the heating section 108 is on.

Figure 4A:
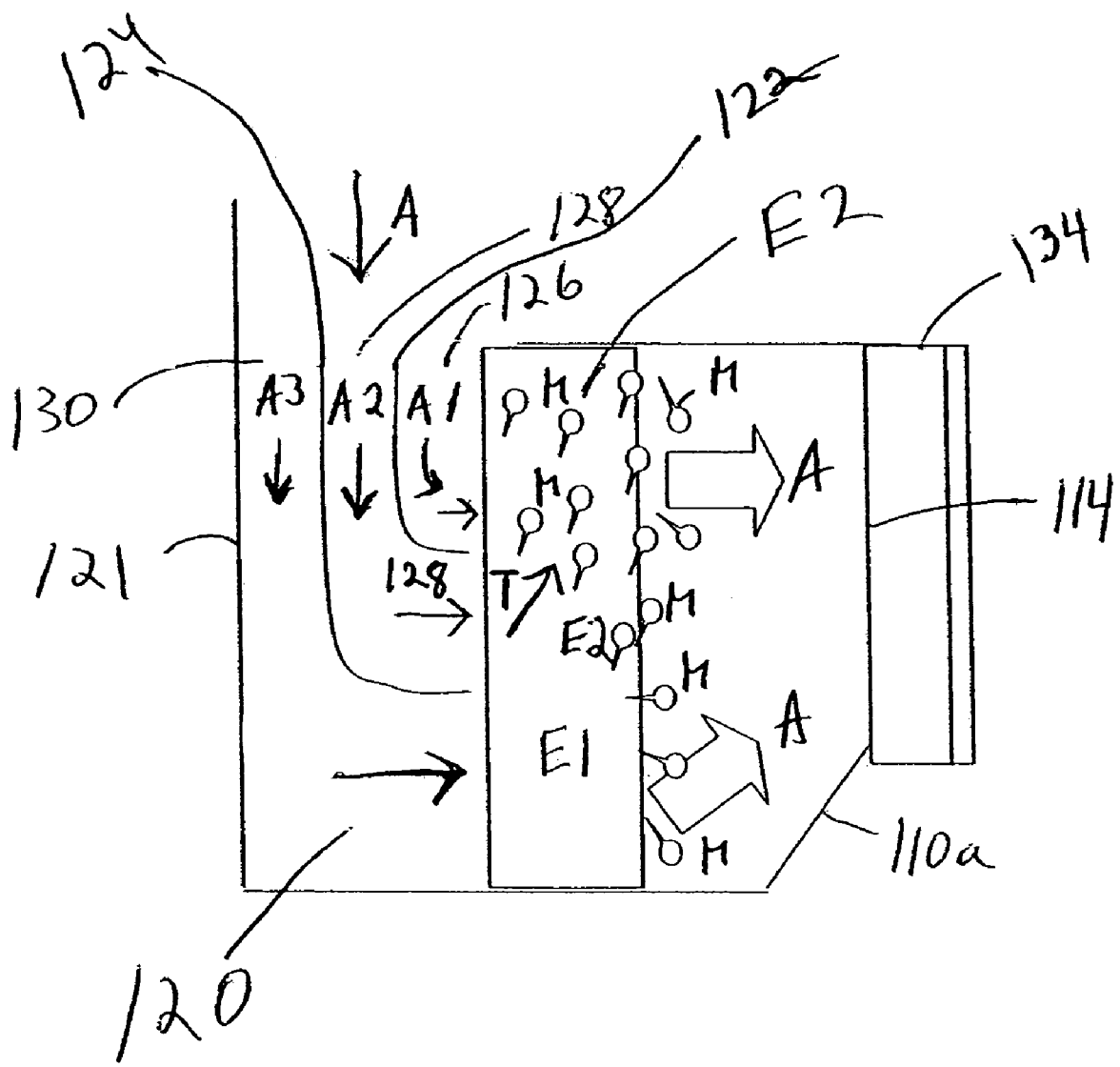
FIGS. 4a-4c are enlarged views of evaporators that may be used in the ADHVAC of FIG. 2, in a variety of configurations, in accordance with an embodiment of the present invention.

In accordance with an embodiment of the invention, this is accomplished by providing more air flow to a lower portion of the evaporator 118 than to an upper portion. FIG. 4a is an enlarged view of the gap 120 and the evaporator 118. The vent 138 is not shown in this view for ease of illustration. The baffles 122, 124 are positioned to direct more air towards a lower portion E1 of the evaporator 118 than towards an upper portion E2. In this example, the baffles 122, 124 are positioned so that about 25% of the air flow A flows along the channel 126, indicated by arrow A1; about 25% of the air flow A flows along the channel 128, indicated by arrow A2; and about 50% of the air flow flows along the channel 130, indicated by arrow A3. Channels 122 and 124 direct the air flow A1 and A2 (about 50% of the air flow) onto the upper portion E2 of the evaporator face 118A. The channel 130 directs the air flow A3, which in this example also comprises about 50% of the air flow A, onto a lower portion E1 of the evaporator face 118a. More air flows through the channel 130 than the other channels 126, 128 because the centrifugal force of the blower 104 drives more air towards the interior wall 121, into the channel 130. In this example, the upper portion E2 is the upper two-thirds of the evaporator 118 and the lower portion E1 is the bottom third of the evaporator. Those dimensions and air flow distributions may vary.

Figure 1C:
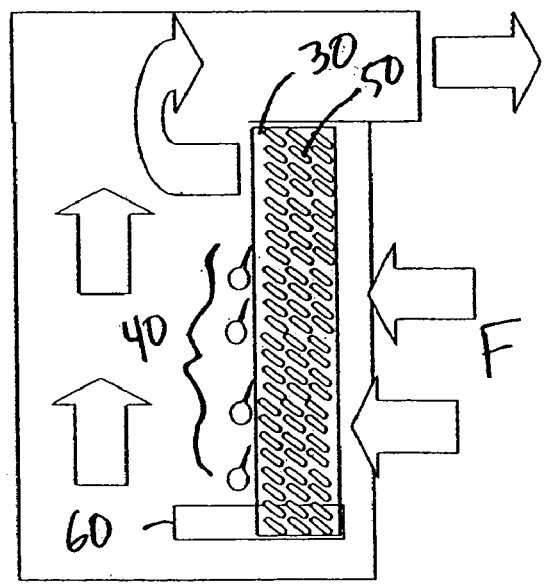

During operation of the AC section 106, air flow through the evaporator 118 forces moisture (indicated by drops "M") off of the evaporator coils (not shown) and gravity draws the moisture downward, as mentioned above. Without being limited to any particular theory of operation, it is believed that since more of the air flow A is directed onto the lower portion E1 of the evaporator 118 then the upper portion E2, higher air pressure is created in the lower portion. The moisture M that would normally be drawn downward by gravity is therefore pushed up by the higher pressure. Instead of moving horizontally (by the air flow), downward (by the force of gravity), and out of the evaporator 118, as in the horizontal evaporator 30 of FIG. 1c, for example, the moisture M moves horizontally and upward, along arrow T, for example, as the moisture follows the path of least resistance through the evaporator 118. The movement of the moisture M in the upper portion E2 of the evaporator 118, transverse to the air flow A1, A2, is believed to slow the air flow through the evaporator. The higher volume of air flow A3 through the smaller volume of the lower portion E1 of the evaporator 118 also causes the overall air flow to slow. The moisture drops M falling down the rear wall of the evaporator 118 may also slow the speed of the air flow A3, somewhat. After exiting the body of the evaporator 118, the moisture drops M fall into a drainage pan (not shown), as described above. Slowing the air flow through the evaporator 118 results in a decrease in the air flow through the entire ADHVAC 100.

Differentially directing air onto the evaporator 118 so that the lower portion E1 of the evaporator 118 is loaded by higher air flow and the upper portion E2 of the evaporator 118 is loaded by moisture M is believed to create a "passive valve" that decreases the air flow through the evaporator during operation of the AC section 106. This enables the AC section 106 to operate efficiently. When the AC section 106 is off, there is no moisture in the evaporator 118 and no restriction of the air flow. The rate of air flow through the heating section 108 when it is on is therefore greater than the rate of air flow through the evaporator 118 when the AC section 106 is on. The reduction in airflow by the evaporator 118 is within the operating cycle of the blower 104, and the air flow A is reduced through the entire device. The blower 104 does not, therefore, overheat due to the backup in air.

Figure 4B:
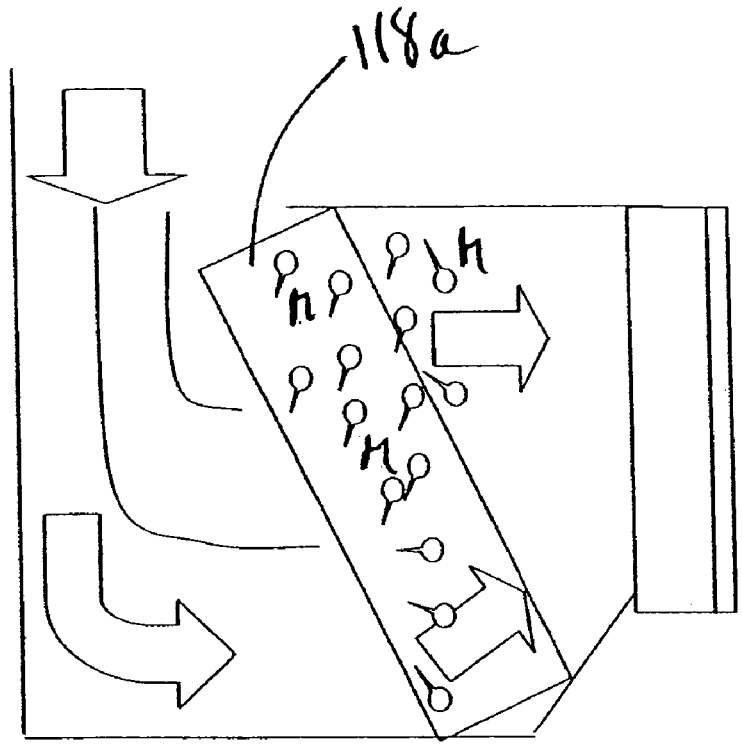
Figure 4C:
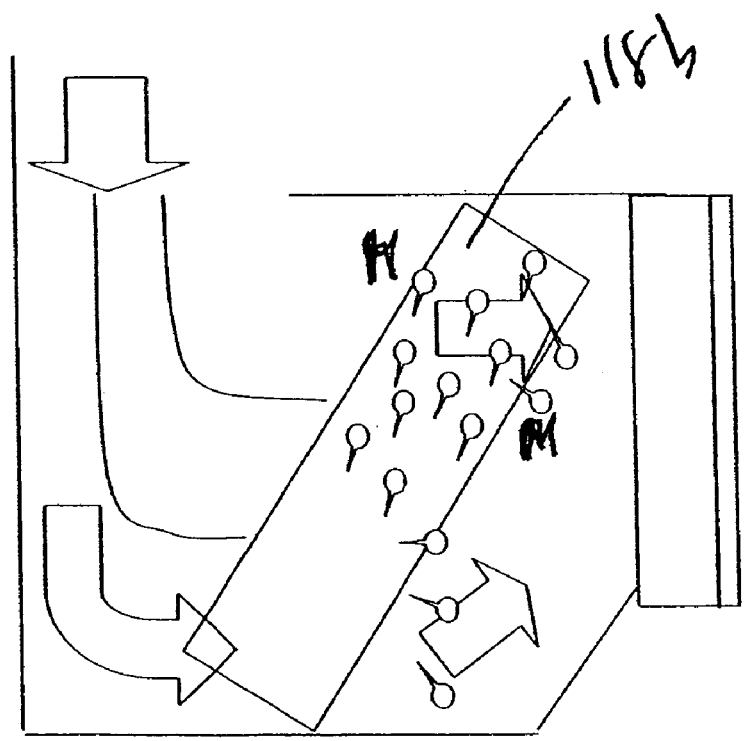

FIG. 4b and FIG. 4c are alternative configurations of the evaporator 118b, 118c, to provide passive valving. In FIGS. 4b and 4c, the evaporators 118a, 118b are transverse to the pathway and to the airflow. The term "transverse" here means that the upstream and downstream faces of the evaporators 118b, 118c through which air flows, are not normal to the direction of the pathway and to the airflow. Tilting the evaporators 118a, 118b as shown is also believed to "load" the evaporator with moisture M by driving the moisture upwards, slowing air flow. In addition, the greater length of the evaporators 118a, 118b, as well as the greater distance that must be traversed by the air through the evaporators, further slows the air flow.

FIG. 5 is a top view of the lower portion of the ADHVAC 100, with the upper portion removed, along line 5-5 of FIG. 2. The plate 119, which covers the gap 120, defines the passage 119a through which the blower 104 forces air into the gap 120. Top edges of the baffles 122, 124, and the channels 126, 128, 130, are shown with more accurate positioning. In this example, the gap 120 has a width "G" of about 8 inches (20 cm), the distance between the evaporator 118 and the first baffle 122 is about 4 inches (10 cm), the distance between the first baffle 122 and the second baffle 124 is about 2.5 inches (6.5 cm), and the distance between the second baffle and the interior wall 121 is about 1.5 inches (3.8 cm).

FIG. 5 also shows more detail of the AC section 106. The condensor section 116 comprises a condensor 150 comprising coils for carrying refrigerant (not shown), as is known in the art. A compressor 152 pumps refrigerant between the coils in the evaporator 118 and the coils in the condensor 150, via tubes 154. If the AC section 106 is to act as a heat pump, a heat pump valve 156 and a check valve 158 are also preferably provided. Vents (not shown) are also provided in the walls of the housing 110, though which air is drawn by the fan 152, to be blown through the condenser 150. Activation of the heat pump valve 156 reverses the direction of the refrigerant, enabling the evaporator 118 to heat air passing through it, as is also known in the art. The AC section 106 may be converted into a heat pump to generate heat instead of or along with the heating section 108, for more efficient operation. Heat pumps, however, cannot operate efficiently at less than 40° F. (4.4° C.). If it is known that an AHDVAC 100 will not be used at temperatures below 40° F. (4.4° C.), the heating section 108 may be the AC section 106 acting as a heat pump, and a separate heating section 108 may not be required.

It is noted that in FIG. 5, the width of the baffles 122, 124 and the resultant chambers 126, 128, 130 are not the same as the width "W" of the evaporator 118, due to the presence of the tubes 154. The width of the baffles 122, 124 and the chambers 126, 128, 130 may be the same as the width "W" of the evaporator 118, which in this example is 22 inches (55 cm), by positioning the tubes 154 differently.

Figure 6A:
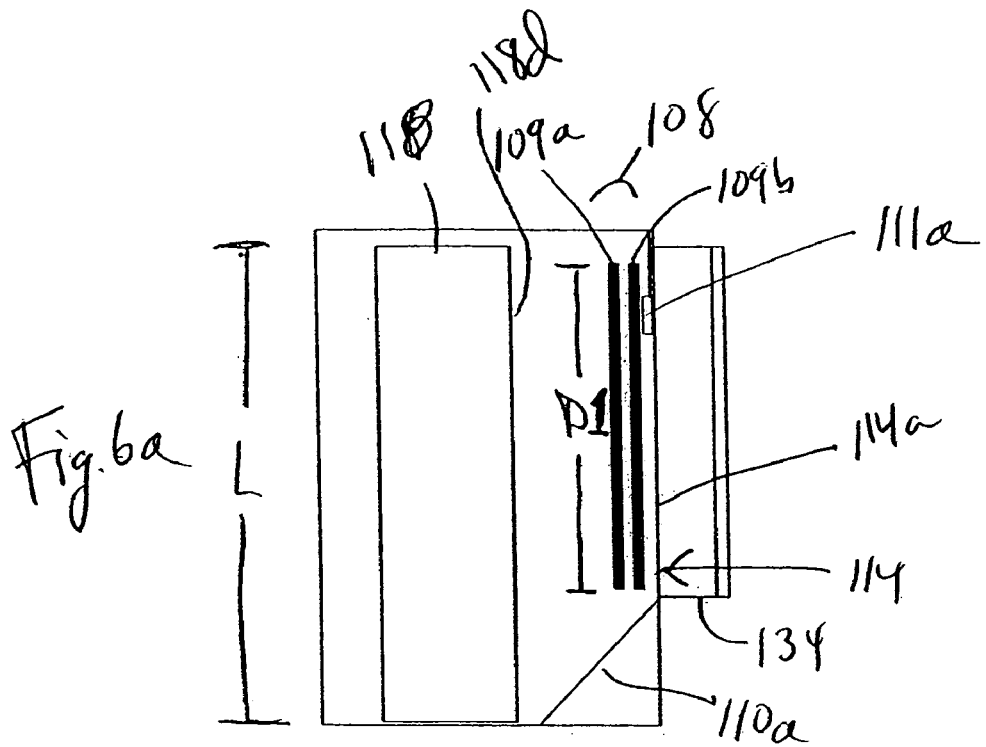
FIG. 6a is a side view of the rear of the ADHVAC, showing the heating section in more detail.

FIG. 6a is a side view of the rear of the ADHVAC 100, showing the heating section 108 in more detail. The heating section 108 comprises one or more heating elements 109 proximate the outlet 114. In this example, two heating coils 109a, 109b are provided. Two temperature sensors 111a, 111b are also provided. The coils may each be 10,000 watt coils, for example. The evaporator 118 is also shown. The diameters D1 of the heating coils 109a, 109b, are preferably about the same as the diameter D2 of an entrance 114a of the outlet 114. In this case the term "about" means that the diameter D1 of the heating coils 109a, 109b is within ±15% of the diameter D2 of the outlet 114. Preferably, being within ±10% is more preferred and being the same within tolerances is most preferred. If the heating coils 109a, 109b have too much greater diameters D1 than the diameter D2 of the outlet entrance 114a, they may overheat. If the heating coils 109a, 109b have a diameter D1 too much less than the diameter D2, the air may not be sufficiently heated. Preferably, the area of the outlet entrance 114a and the area of the heating elements 109a, 109b are also less than the surface area of a downstream face 118d of the evaporator 118, though which air exits the evaporator. While preferred, such a configuration, for the heating section 108 is not required.

Figure 6B:
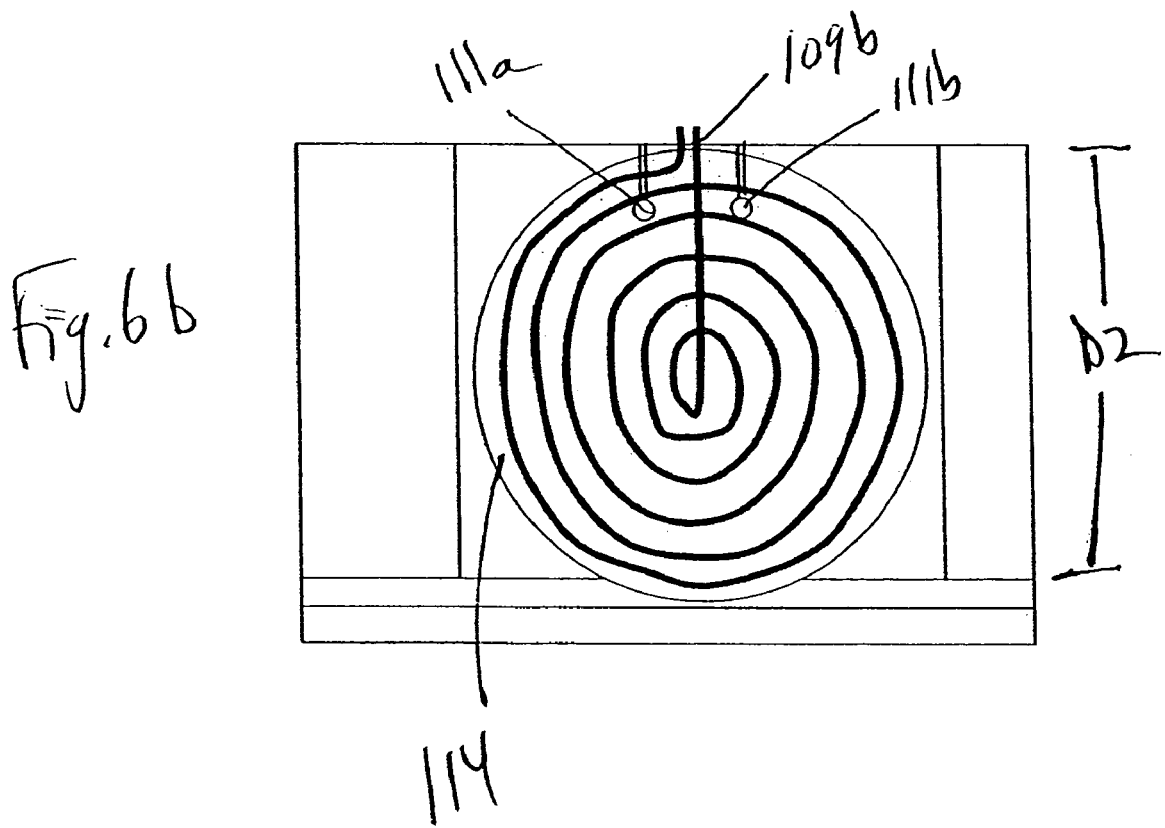
FIG. 6b is a view of the outlet from outside of the ADHVAC.

FIG. 6b is a front view of the outlet 114, which in this example is circular. The front coil 108b is shown in this view, behind the outlet 114. The coils 109a, 109b are both wound into a circles having about the same diameter "D1" (FIG. 6a) as the diameter "D2" (FIG. 6b) of the circular outlet 114. Conventional straight coils may be wound into the desired shape and size. Pre-wound coils may be obtained from Ningbo Hicon International Industry Co., Ltd, Cixi Ningbo, China, for example. Since the area defined by the entrance 114a of the outlet 114 is less than the surface area of the downstream face 118d evaporator 118, air A exiting the evaporator 118 converges as it flows past the coils 109a, 109b and out the outlet 114. (See FIG. 4a.) This is facilitated by the tapered edge 110a in the housing 110. The velocity of the air A is thereby increased as the air approaches the outlet 114. The higher velocity improves the heat transfer from the coils 109a, 109b to the air, improving heat absorption by the air and cooling of the coils. Overheating of the coils 109a, 109b is thereby avoided. The heating capacity of the heating section 108 may thereby be increased as compared to conventional heating units having the same air flow. In one example, the heating capacity is increased from about 50% to about 70% as compared to prior art heating devices, which typically have limited air flow.

As mentioned above, the outlet 114 may have other shapes besides circular. Regardless of the particular shape, the area defined by the entrance 114a to the outlet 114 and the area occupied by the heating coils 109a, 109b, or other such heating elements, are preferably about the same, and are less than the surface area of the downstream face 118d of the evaporator 118. In one example, the outlet 114 and the heating coils 109a, 109b have diameters of about 14 inches (36 cm) and areas of about 154 square inches (1,000 cm$^2$). The evaporator 118 has a downstream face 118d having a length L of about 22 inches, a width W of about 13 inches, and an area of about 286 square inches (1,800 cm$^2$).

The temperature sensors 111a, 111b are preferably provided proximate the heating coils 109a, 109b to monitor for overheating. The ADHVAC 100 may be set up to automatically shut off the heating coils 109a, 109b if the temperature in the heating section 108 exceeds 200° F. (93° C.), for example. This may be controlled by a processor, such as the microprocessor 215 discussed herein, or a simple switch. While not preferred, the heating section 108 could also comprise oil or gas burning heaters instead of electrical heating elements.

FIG. 7a is a front view of an ADHVAC 100, showing the inlet 112 and an inlet vent 136 to enable creation of a positive pressure within the PIE 200. The vent 136 comprises an opening 136a through the housing 110 to the airpath. A sliding damper 137 (shown in phantom) is in the interior of the housing 110 to selectively open and close the vent 136. In FIG. 7a, the vent 136 is in a closed position. The damper 137 has portions extending through guide slots 139a, 139b and out of the housing 110. The guide slots 139a, 139b support and guide movement of the sliding damper 137. Knobs 139c, 139d are attached to the members, outside of the housing 110, for engagement by an operator. The sliding damper 137 may also be coupled to a motor (not shown) for automatic movement under the control of an operator, a switch, or a processor, such as the microprocessor 215. An exhaust opening 168 of the condenser 150 is also shown.

Figure 7B:
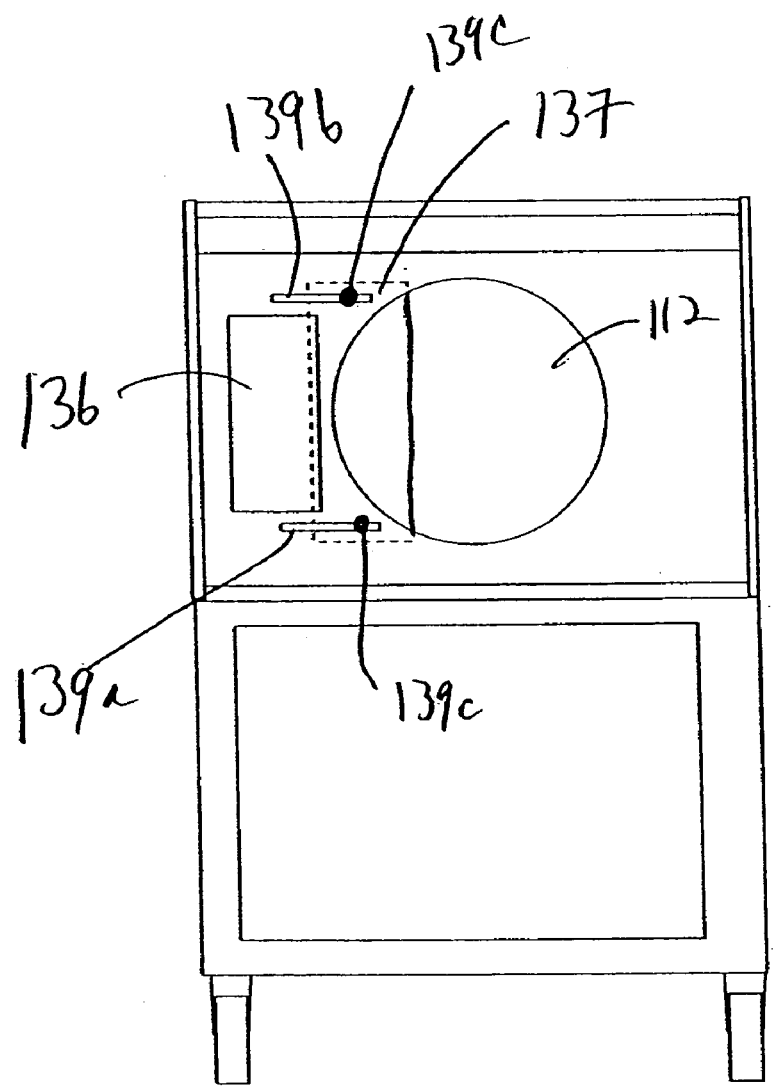

In FIG. 7b, the sliding damper 137 is shown moved to the right, to open the vent 136. Preferably, when the damper 137 is moved to the open position, it also closes a portion of the inlet 112, to block some of the air coming from the PICS 200 from entering the inlet, as shown. The damper 137 may have an opened and closed position, or the extent to which the vent 136 is opened may be selectively varied.

As mentioned above, an adjustable outlet vent 138 is also preferably provided in the gap 120, as shown in FIG. 2, to enable creation of a negative pressure within the PIE 201 by diverting air withdrawn from the PIE, from being returned to the PIE. It is preferred that the second air portioning vent 138 be downstream of the air decontamination section 102, so that the air is decontaminated prior to release, and upstream of the AC and heating sections 106, 108, so that air not returned to the PIE is not further processed, for improved efficiency. The second adjustable air portioning vent 138 may be within the exhaust duct collar attachment 134, instead. The damper 139a is movably supported in a single slot 139b extending through the housing 110. A portion of the damper 139a may extend through the slot 138a, out of the housing 110. The portion may have a knob 139b on its end for engagement by an operator, as described above with respect to the damper 127. The damper 139a may also be coupled to a motor for automatic movement under the control of a switch or a processor, such as the microprocessor 215. The damper 139a may have an opened and closed position or the extent to which the vent 138 is opened may be selectively varied.

Figure 8A:
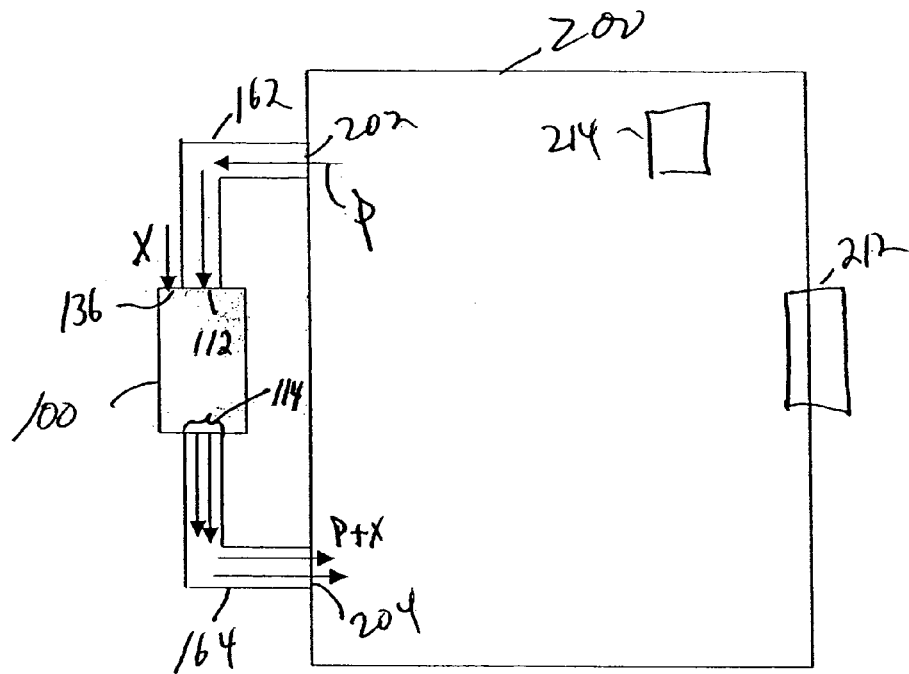
FIG. 8a and FIG. 8b are schematic diagrams of the inlet and the outlet of the ADHVAC of FIG. 2 coupled to a PIE of FIG. 3, arranged to cause positive and negative pressure inside of the PIE, respectively.

FIG. 8a is a schematic diagram of the inlet 112 and the outlet 114 of an ADHVAC 100 coupled to a PIE 201 via the respective ducts 162 (see FIG. 3), arranged to cause positive pressure inside of the PIE. Air P is drawn from the tent 200, through the duct 162, and into the ADHVAC 100 for processing. Processed air exits the ADHVAC 100 and is returned to the PIE 201 via the duct 164. In the positive pressure application of FIG. 8a, the inlet vent 136 near the inlet 112 is opened to draw in external air X. The combined air flow (P+X) into the ADHVAC 100, comprising the external air X and the air P drawn from the interior of the PIE 201, is decontaminated, cooled, or heated, if necessary, and blown back into the PIE 201. Since more air is blown into the PIE 201 than is drawn out (due to the addition of the external air X), the pressure within the PIE 201 increases. The vents 212 in the PIE 201 allow excess air to exit when the pressure rises above a predetermined level, as mentioned above. The vents 212 may be manually set to allow a predetermined leakage. The vents 212 may also be automatically adjusted based on the pressure sensor 214 within the PIE 201. The microprocessor 215 controls the operation of the PIE vents 212, as well. A switch may be used, instead. When a positive pressure is created in the PIE 201, outside air, which may be contaminated or may merely contain normal air that may be threatening to patients with suppressed or weakened immune systems, is less likely to enter the PIE. Positive applications may also be used where certain medical procedures, such as surgical procedures, or in a temporary pharmacy, for example. A positive pressure of at least +0.01 inch (0.25 mm) water column may be established, in accordance with standards established by the Centers for Disease Control and Prevention ("CDC"). Preferably, a positive pressure of about +0.03 inches (0.76 mm) water column is established.

Figure 8B:
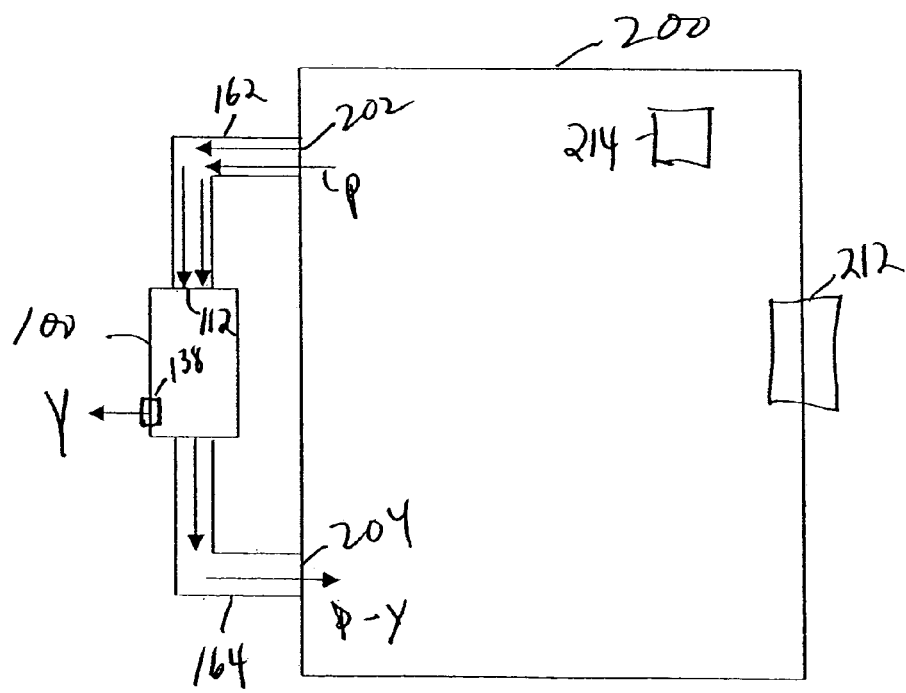

FIG. 8b is a schematic diagram of an ADHVAC 100 coupled to a PIE 201, in a negative pressure application. The outlet vent 138 is opened, allowing air to exit from the ADHVAC 100, indicated by arrow "Y". Air P-Y is therefore returned to the PIE 201. Since less air (P-Y) is returned to the PIE 201 than is withdrawn (P), the pressure inside the PIE 201 is decreased. As above, the vents 212 may be manually operated or sensor controlled. When a negative pressure is created in the PIE 201, the air within the PIE, which may be contaminated by infected patients, is less likely to escape. A negative pressure of −0.01 inches (−0.25 mm) water column may be established in accordance with CDC standards. Preferably, a pressure of −0.02 inches (−0.51 mm) water column is established.

The ADHVAC 100 may switch from causing positive pressure in the PIE 201 to causing negative pressure, and vice-a-versa, by changing the states of the vents 136, 138 by appropriate movement of the respective dampers 137, 139a. In one example, a negative pressure may be established in the PIE 201 first, to prevent escape of infectious diseases. The pressurization may then be switched to a positive pressure to prevent contamination from the outside. This may be required if a medical procedure, such as surgery, needs to be performed, for example.

The establishment of negative pressure inside the PIE 201, minimizing the risk of escape of contaminated air from the PIE, has been found to be the most common scenario. Less negative pressure can be tolerated when temperatures are less than 32° F. (0° C.), since biological agents that may escape will not survive below freezing temperatures. Spores, such as anthrax spores, in contrast, can survive the cold. In the summer, when biological agents will survive, higher negative differential is needed to decrease the risk of escape.

It is noted that opening the outlet vent 138 to create a negative pressure in a PIE 201 may cause a pressure drop and air flow drop that assists in the operation of the AC section 106. On the other hand, a positive pressure in the tent may increase the resistance to air flow through the unit, decreasing the air flow through the air conditioning portion 106.

In accordance with another embodiment, a PICS system 200 comprises multiple PIEs 201 coupled to each other. Each PIE 201 may be coupled to a separate ADHVACS 100. FIG. 9 is a top schematic view of a first PIE 201*a* coupled to a second PIE 201*b*. The first PIE 201*a* could house patients and the smaller, second PIE 201*b* could house health care professionals, for example. Preferably, a chamber 201*c*, such as a vestibule, is provided between the first PIE 201*a* and the second PIE 201*b*, to allow for passage between the first and second PIEs, with minimal contamination and pressure loss. In this example, the first PIE 201*a* is under positive pressure, as indicated by the outwardly pointing arrows within the PIE 201*a*, and the second PIE 201*b* is under negative pressure, as indicated by the inwardly pointing arrows outside of the PIE 201*b*. The positive pressure prevents or mitigates the entry of outside air and air in the vestibule 201*c* into the PIE 201*a*. Entry of air from the PIE 201*b* is also limited. Such an arrangement may be appropriate if the patients have suppressed immune systems, so that infectious diseases do not enter the PIE 201*a*, for example. Alternatively, a negative pressure may be established in the PIE 201*a* and a positive pressure in the PIE 201*b*, to prevent the escape of infectious diseases from the PIE 201*a* to the outside and to the PIE 201*b*. Both PIE 201*a* and PIE 201*b* may be pressurized in the same way, or not pressurized at all, as well.

The vestibule 201*c* may have openings 225 for entry and exit by personnel, which are coupled to respective doors 226 of the PIE 201*a*, 201*b*. The doors 226 of the PIEs 201*a*, 201*b* may comprise a conventional door comprising aluminum covered by vinyl. The door may be supported in a door frame defined by the PIE 201, by hinges. The doors 226 can also comprise a plastic curtain. Both a door and a plastic curtain may be provided for additional protection against unwanted air passage and possible contamination. An ADH- VAC 100 may also be coupled to the vestibule, to provide air decontamination, ventilation, heating, and/or cooling, for even further protection. A positive or negative pressure may then be created in the vestibule, as well. While preferred, vestibules 201c are not required. Adjacent PIEs 201a, 201b may be connected directly to each other with doors and/or curtains between them.

The larger PIE 201a, which in this example has dimensions of 19 feet (5.8 m)×35 feet (10.7 m)×11 feet (3.4 m), as discussed above, includes internal ducting 206, as shown in FIG. 3. The smaller PIE 201c, which in this example has dimensions of 19 feet (5.8 m)×19 feet (5.8 m), does not need such ducting, although that is an option.

Figure 10:
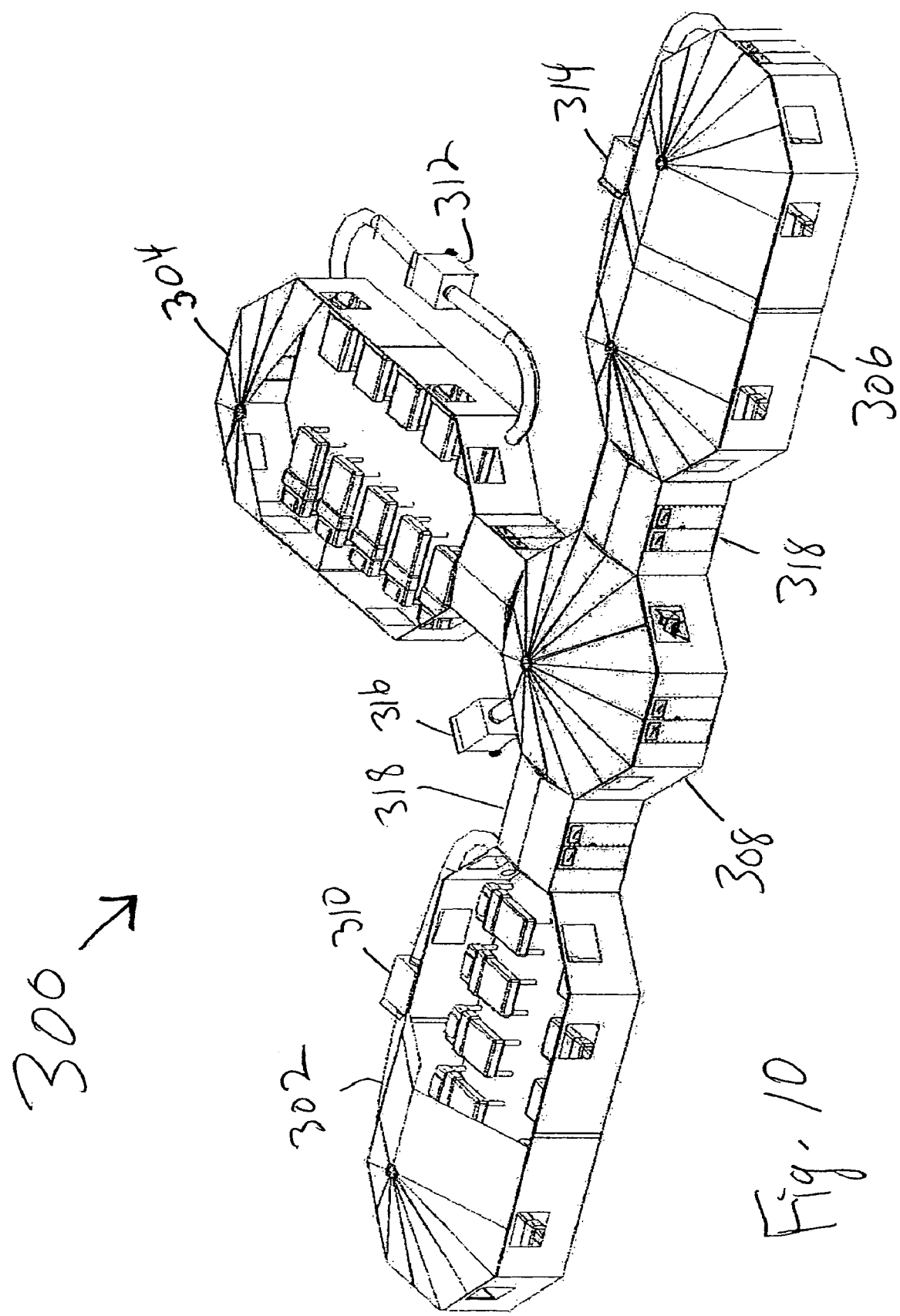
FIG. 10 is a perspective view of a portable isolation containment complex comprising three large PIEs coupled to a smaller PIE.

FIG. 10 is a perspective view of a PICS complex 300 comprising three large PIEs 302, 304, 306 coupled to a smaller PIE 308. The PIEs 302 and 304 partially cut away to show their interiors. Each PIE 302-308 is coupled to a respective ADHVAC 310, 312, 314, 316. Vestibules 318 are preferably provided between the smaller PIE 308 and each of the larger PIEs 302-306 to further mitigate air flow and possible contamination between units, as discussed above. The smaller PIE 308 in this example acts as a transition hub between the large PIEs 302-306. Medical personnel and/or command and control personnel may work in the smaller PIE 308, while patients reside in the larger PIEs 302-306. The pressure in the smaller PIE 308 will typically be different than the pressures in the larger PIEs 302-308, although that is not required. For example, the larger PIEs 302-306 may all be in a negative pressure state while the smaller PIE 308 may be in a positive pressure state, or vice-a-versa. The larger PIEs 302-306 may also be in different pressure states with respect to each other, depending on the use of each PIE.

In accordance with another embodiment of the invention, air flow to the evaporator 118 is varied by mechanical means, instead of the "passive valve" described above. FIG. 11 is a schematic diagram of an ADHVAC 400 including a sliding damper 402. The damper 402 is driven by a motor 404 coupled to the damper by a screw drive 406, for example. The damper 402 may be moved to cover a portion of the gap 120 when the air conditioning section 106 is on, to reduce the air flow. The motor 404, which may be a servo motor or a stepper motor, for example, operates the screw drive 406 to open and close the damper 402. When the heating section 108 is on, the gap 120 is completely open. The baffles 122, 124 are preferably provided to guide the air to the evaporator 118; however, the baffles 122, 124 are preferably more evenly spaced to provide more even distribution of air across the evaporator 118. The motor 404 may be controlled by a processor, such as the microprocessor 215, which may activate the motor to partially close the gap 120 when the AC section 108 is activated. A switch may be used instead. The switch may be manually operated, as well. The damper 402 may be manually controlled by a crank, or if the screw drive 406 is replaced by a control rod extending out of the housing 110, directly by hand. Certain other components common to the ADHVAC 100 of FIG. 2 are commonly numbered.

In another alternative for adjusting airflow through the evaporator when the AC section 106 is on, the speed of the blower 104 may be reduced at that time.

As mentioned above, a processor, such as the microprocessor 215, may control operation of the components of the ADHVAC 100. The microprocessor 215 may be coupled to the thermostat and the sensors to monitor and adjust parameters of the ADHVAC 100 and the PIE 201. A remote console (not shown) may be provided in the PIE 201, coupled to the microprocessor 215, to display system parameters, indicate problems, and allow for input of information. As mentioned above, a thermostat 214 and pressure sensor 216 may be provided in the PIE 201, coupled to the microprocessor 215, to monitor the temperature and pressure in the tent. The microprocessor 215 may also be coupled to motors coupled to the first and second vents 136, 138 to enable automatic adjustment of the positive or negative pressure in the tent, based, at least in part, on signals provided by the pressure sensor 216.

Sensors (not shown) may also be provided in the ADHVAC 100 to monitor air flow across the filter 102a, and operation of the blower 104 and the UV lamps 102b, for example. A light, bell or other indicator may be activated if an operating parameter goes beyond an acceptable threshold, for example.

The microprocessor may also be programmed to control the operation of the blower 104, the inlet vent 136 and the outlet vent 138 to maintain a desired pressure in the PIE 201. For example, if a positive pressure is to be maintained in the PIE 201 and the microprocessor 215 determines that signals from the pressure sensor 216 indicate that the pressure is dropping below a threshold, the microprocessor 215 may increase the opening of the inlet vent 136 by activating a motor coupled to the sliding damper 137.

If a negative pressure is to be maintained within the PIE 201 and the microprocessor 215 determines from the signals received from the pressure sensor 216 indicate that the pressure has risen above a threshold, the microprocessor 215 may increase the opening of the vent 138 by activating a motor coupled to the sliding damper 139a. In addition, to ensure that the desired rate of air exchanges is maintained, if the blower 104 is a variable speed blower, blower speed may be increased.

In another example, the microprocessor 215 may control, or assist in the control of, air flow through the evaporator 118. When signals from the thermostat 214 indicate that the temperature is above a threshold, the microprocessor 215 may turn on the AC section 106 and lower the speed of the blower 104, decreasing air flow through the evaporator 118, for example. The microprocessor 215 may also control the damper 402, as discussed above.

The microprocessor 215 can also control operation of the heating section 108 and cause the AC section 106 to operate as a heat pump, based, at least in part, on the external temperature.

As discussed further below, ozone may be generated by the ADHVAC 100 for flooding a PIE 201, for example. The length of time that ozone is generated and dispersed through the PIE 201 may be based on the parts per million (PPM) hours exposure for established kill rates for a particular contaminant. The microprocessor 215 may control the length of time the ozone is generated.

These are merely examples of processor control of the air processing devices of the present invention. Other examples are discussed herein and would be apparent to those skilled in the art.

The microprocessor 215 may be programmed by software stored in memory 215a. Programs could be implemented in whole or in part by hardware, as well. An application specific integrated circuit may be used, for example. Processor control of this operation of the ADHVAC 100 and IHVAC 400a, 400b minimizes problems due to human error. The processor may be a computer, as well.

Figure 9:
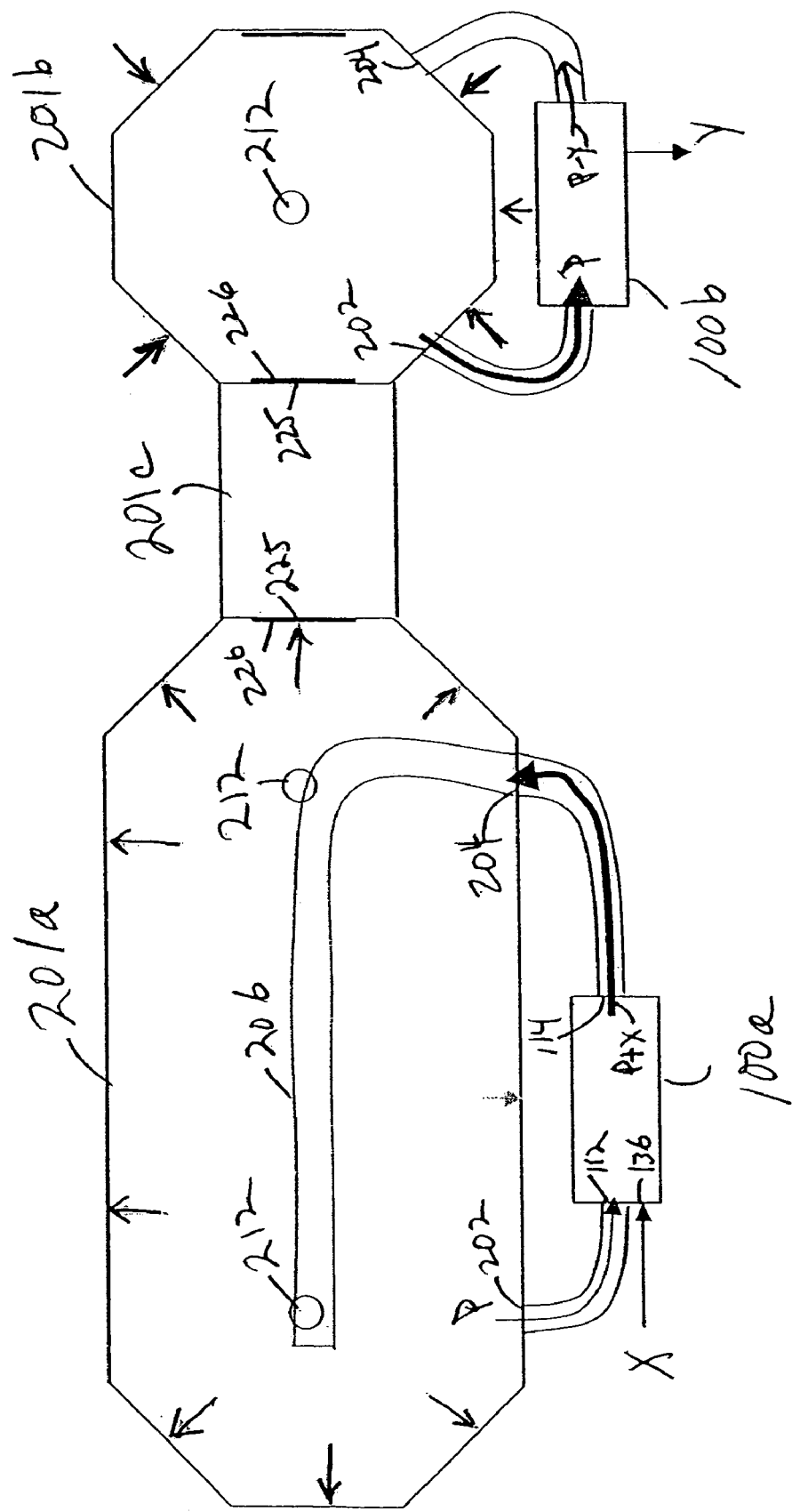
FIG. 9 is a top schematic view of a first PIE coupled to a second PIE, in accordance with an embodiment of the invention.

The PIE 201 may be constructed of aluminum, such as 6063-T5 and 6061-T6 aluminum, for example, which is readily commercially available. An insulated cover set may be provided to aid effective cooling and heating in extreme environments. The cover set may have a rating of R3 in accordance with American Society of Heating Refrigerating Air Conditioning Engineers (ASHRAE). A vinyl sheet may be used to cover the insulated cover set. Integral fluorescent light and wiring harness kit may be provided for lighting and electrical functions inside the PIE 201. An appropriate tent may be obtained from Design Shelter, Inc., Mississauga, Ontario, and its distributor Western Shelter Systems, Eugene, Oreg., for example, which accommodate a temperature range of −40° F. (−40° C.) to +140° F. (60° C.). The larger PIE 201a in FIG. 9 provided by these companies weighs about 860 pounds (390 kg) while the smaller PIE 201b weighs about 800 pounds (363 kg).

Other tents and other types of portable structures may be used, as well. For example, the PIE may be a trailer, which have been used as mobile emergency treatment care facilities by the military and first responders as a rapidly deployable, semi-permanent facility. While the PIE is preferably portable, it may be a permanent or semi-permanent structure once assembled. The ADHVAC 100 may also be used to isolate all or parts of permanent structures, such as individual rooms or groups of rooms in buildings. The room or rooms may be isolated from a building's air systems, which may be replaced by the ADHVAC, if needed.

In one example, an ADHVAC 100 in accordance with embodiments of the present invention, having an AC section 106 with a rating of 36,000 BTUs (9,100 kcal) for temperate climates (temperature range of from about 0° F. (78° C.) to about 100° F. (38° C.)), may weigh about 385 pounds (175 kilograms). In another example, an ADHVAC 100 in accordance with embodiments of the present invention, having an AC section 106 with a rating of 60,000 BTUs (15,000 kcal) for extreme climates (temperature range of from about −20° F. (−11° C.) to about +120° F. (48° C.)), may weigh about 500 pounds (227 kilograms). The 36,000 BTU (AC) rated ADHVAC 100 may be powered by a 12 kw generator. The 60,000 BTU (AC) rated ADHVAC 100 may be powered by a 22 kw generator. The 12 kw generator may weigh about 550 pounds (250 kg) while the 22 kw generator may weigh about 1,000 pounds (454 kg). Portable commercial generators of these powers are commercially available. One or more generators 175, ADHVACs 100, and PIEs 201 may be readily transported to a site by truck, trailer, or helicopter, for example. They may also be conveyed by a transport plane. They may be dropped to a site by parachute, as well. The ADHVAC 100 and the generator 175 may be rolled into position by an operator using the handles 142.

As discussed above, in another aspect of the invention, an air processing device comprises only heating and air conditioning sections. FIGS. 12a and 12b are examples of IHVACs 400a and 400b in which certain components common to the ADHVAC 100 of FIG. 2 are commonly numbered. The inlet 112 may be positioned as shown in FIGS. 12a and 12b, or on other sides of the blower 104. In the IHVAC 400a, the blower 104 is above the air conditioning section 106 and the heating section 108. In the IHVAC 400b, the blower 104, the air conditioning section 106 and the heater 108 are stacked linearly. While the IHVAC 400b is shown stacked vertically, the components may be arranged horizontally, as well. Passive or active valving is provided to decrease the air flow through the air conditioning section 106 when on, as discussed above. In this case, the blower section 104, air conditioning section 106 and heater section 108 can be accommodated within a smaller casing. If adjustable air positioning vents are provided, as described above, the IHVAC 400a, 400b could provide positive or negative pressure in the PIE 201, as well.

In accordance with another embodiment of the invention, the air conditioning section 106 and the heating section 108 of the ADHVAC 100 of FIG. 2 are not included, and an air decontamination device, such as the air decontamination device described in the '041 application and the '1041 publication, which are incorporated by reference herein, is coupled to a PIE 201 in a PICS 200. Positive and negative pressure may be established in the tent by blowing air into the tent or drawing air out of the tent, as described herein and in the '041 application and the '1041 publication. A preferred air decontamination device is available from FailSafe Air Safety Systems Corp., Tonawanda, N.Y.

Figure 13A:
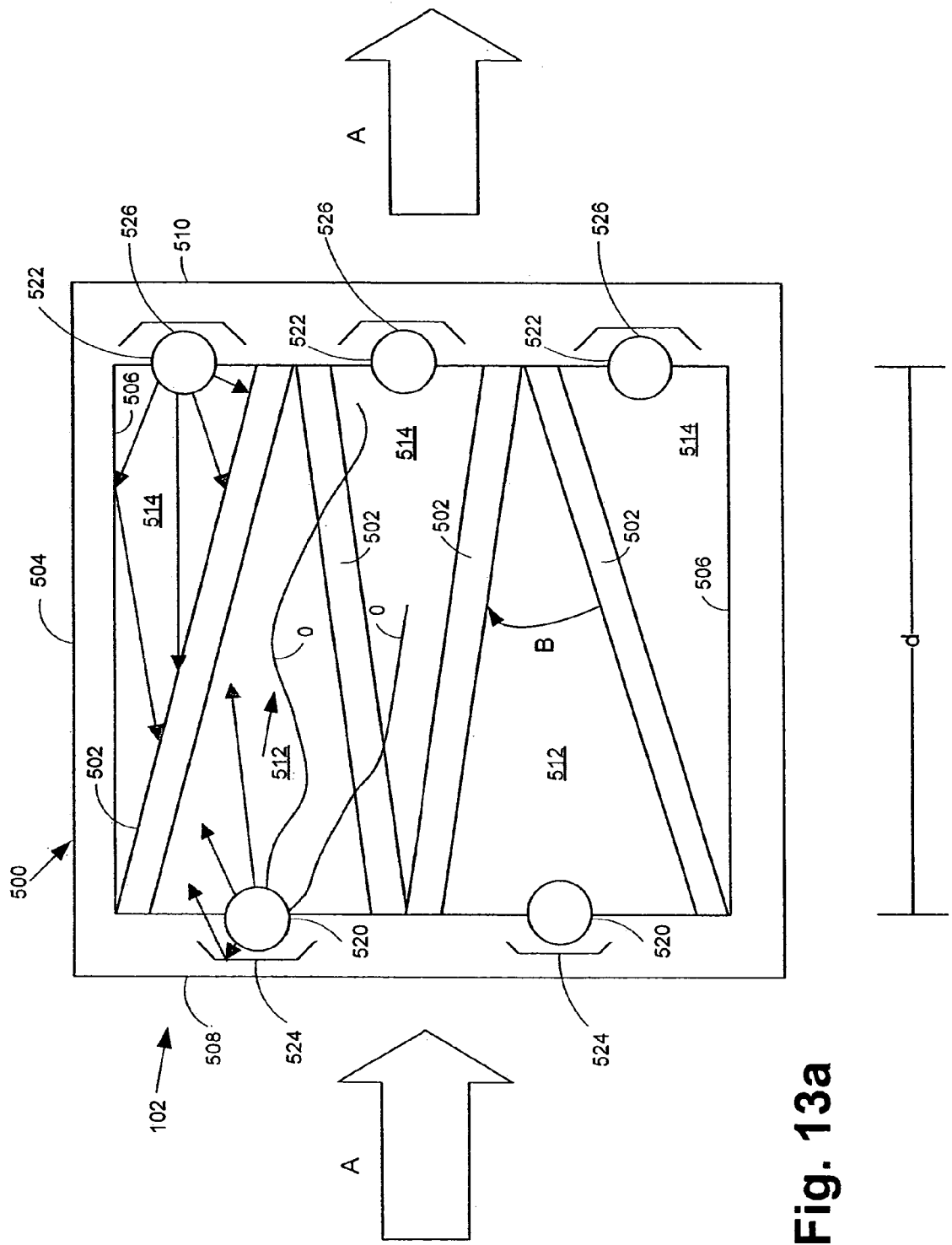
FIG. 13a is a schematic representation of a preferred air decontamination section for use in ADHVAC of FIG. 2.

FIG. 13a is a schematic representation of a preferred air decontamination section 102 for use in ADHVAC 100. The air decontamination section 102 comprises a V-bank filter 500 comprising a plurality of transverse intersecting walls 502. The filter 500 is supported in a filter case 504 with top and bottom walls and two side walls. Preferably, a surface 506 of the filter case 504 facing the filter media is reflective to ultraviolet ("UV") light. For example, the surface 506 may be aluminum. Air flow A enters the upstream side 508 of the filter 500 and exits the downstream side 510 of the filter. The transverse intersecting walls 502 define upstream facing, open faced V-shaped chambers 512. Downstream facing, open faced V-shaped chambers 514 are defined by the walls 502 and the filter walls of the casing 504. The open faced chambers 512, 514 may be defined by a filter wall or walls having other configurations, as well. Each V-shaped region 512, 514 may extend over an arc B of about 30 degrees. The depth of the V-shaped regions may be about 11½ inches (29.2 cm), for example.

UV lamps 520 upstream of the filter 500 and UV lamps 522 downstream of the filter are preferably supported at least partially within the upstream facing chambers 512 and the downstream facing chambers 514 of the filter 500. The ultraviolet lamps 520, 522 preferably provide ultraviolet germicidal irradiation ("UVGI") "R" at germicidal levels at the filter surfaces 500a, 500b. Radiation R is only shown being emitted by the upper UV lamps 520 and 522, for ease of illustration The other UV lamps 520, 522 emit radiation R, as well. UVGI is in a range of from about 2250 to about 3020 Angstroms for air/surface disinfection and sterilization. Reflectors 524, 526 are provided outside of the chambers 512, 514 but close to the UVGI lamps 50, 54, to direct and concentrate UV germicidal irradiation (UVGI) R emitted in a direction away from a respective chamber toward the chamber, improving the germicidal effect of the UVGI in the filter media. The ultraviolet lamps 520, 522 and/or the reflectors 524, 526 may be supported by the filter case 504 or by the housing 110 of the ADHVAC 100. Examples of germicidal UV lamps include PerkinElmer Model GX018T5VH/Ultra-V, Perkin Elmer Optoelectronics, Salem, Mass., for example. The positioning of the UV lamps 522, 524 and the reflectors 524, 526 enable complete and continuous illumination of the media surfaces of the upstream side 508 and downstream side 510 of the filter 500, respectively, during operation.

The upstream UV lamps 520 may also be ozone generating lamps. The air flow A pulls the ozone "O" through the filter 500, increasing the germicidal effect through the filter. Ozone O is only indicated for the upper UV lamp 520, for ease of illustration. The lower UV lamp 520 could emit ozone O, as well. The entire filter 500 may then become a germicidal killing zone through its entire depth. Additionally, ozone facilitates the breakdown of odorants and some toxic gases, further decontaminating the air passing through the filter 500. The downstream lamps 524 may be ozone generators, as well. An example of an acceptable ozone generating UV lamp is a Model GX018T5L/Ultra-V manufactured by Perkin Elmer Optoelectronics, Salem, Mass. 01970 USA. Alternatively, the UV lamps 520 and/or 522 need not be the ozone generators. Many types of ozone generators, such as corona wires, are known and readily available, as described in the '041 application and the '1041 publication.

If ozone generators are provided, the UV lamps 524 downstream of the filter 500 may produce UV radiation R at wavelengths that facilitate the breakdown of ozone. Ultraviolet radiation in the UV "C" spectrum may be used. 255.3 nanometers is an effective wavelength, to break down ozone, for example. Ozone O is not generated while a PIE 201 is occupied.

Preferably, the filter 500 is a high efficiency filter, which traps at least 90% of particles of 0.3 microns. More preferably, the high efficiency filter 12 is a high efficiency particle arresting ("HEPA") filter that traps 99.97% of particles at 0.1 microns, at 1000 CFM (28 CMM). Most preferably, the filter 12 is an ultra high efficiency particulate arresting ("ULPA") filter that traps 99.99% of particles at 0.1 microns, at 2400 CFM (68 CMM). The filter 500 also preferably comprises a fire resistant filter media of such fiberglass. Fiberglass is also translucent to ultraviolet ("UV") light. Transmission of the UV light into and through the filter 12 is thereby facilitated. Some UV light is scattered by the translucent fiberglass, as well. UV light passing into and through the fiberglass media irradiates pathogens on the surface and trapped inside of the filter media. It is believed that the filter 500 slows the movement of contaminants in the air, providing more time for biological agents to be killed by the UV radiation R and the ozone O (if provided), in the filter 500.

Figure 13B:
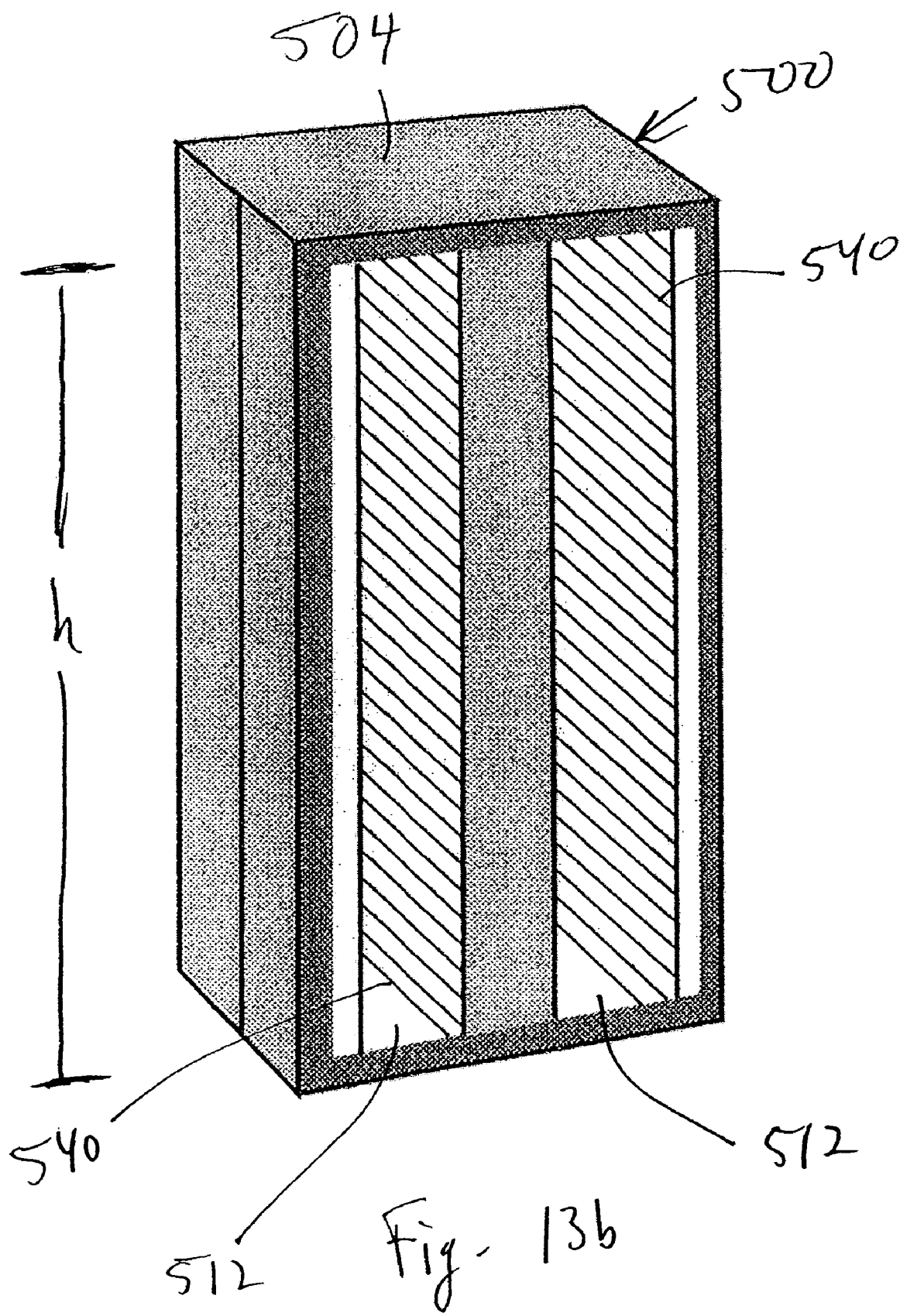

The folds in the media of the V-bank filter 500 are preferably perpendicular to the lengths of the UV lamps 520, 522, for better illumination of the filter media. FIG. 13*b* is a front perspective view of a V-bank filter 500 showing the folds 540 in the media along the lengths of each V-shaped chamber 512. The UV lamps 520 are partially within each V-shaped chamber 512 and extend along the height "h" of each chamber. The rear V-shaped chambers 514 have the same configuration. Such V-bank filters are commercially available from Camfil Farr, Inc. ("Camfil Farr"), Riverdale, N.J., for example, described below. The information below is provided from Camfil Farr literature.

An example of an appropriate V-bank filter is the Camfil Farr Filtra 2000(™) Model No. FA 1565-01-01, available from Camfil Farr, which comprises microglass fiber in an acrylic resin binder. The filters have a pleat depth of 27.5 millimeters. The Filtra 2000(™) may be used in an air decontamination section 102 with an airflow of 1,100 CFM (31 cubic meters per minute), at 1.2 inches (30 mm) water column. This model has a 99.99% efficiency at 0.3 microns, when evaluated according to the IEST Recommended Practice. It has a rated check airflow of 900 CFM (25.48 CMM), at 1.0 inches (25 mm) water column. The media area is 174 square feet (16.16 square meters). The dimensions of the filter are 24 inches×24 inches×11.50 inches (length×height×depth) (0.61 meters×0.61 meters×0.29 meters). FIG. 13*b* is a perspective view of this model.

Camfil Farr 2000(™) Model Nos. FA 1565-02-01, which is an ULPA filter providing 99.999% efficiency at 0.3 microns and 99.99% efficiency at 0.1 microns, may also be used. The dimensions and resistance at airflow of this model and the model described above are the same. The FA 1565-02-01, which has the same media area as the FA 1565-01-01 discussed above, has an airflow of 693 CFM (20 CMM) and may be used in an air decontamination section 102 with an airflow of about 1,100 CFM (31 CMM), for example.

It may also be desirable to flood a PIE 201 with ozone O, as mentioned above, for further decontamination and/or odor reduction in the PIE. This may be done prior to occupation or after occupation. Ozone O is not generated while a PIE 201 is occupied. The UV lamps 522, 524 and/or one or more additional ozone generators supported in the housing along the air path may be used to produce ozone that is exhausted from the ADHVAC 100 through the outlet 114 and ducting 164, into the PIE 201. In this case, if the UV lamps 524 emit radiation in a range that would break down ozone, they would not be turned on. The UV lamps 524 that break down ozone may be controlled by a separate switch or other such manual control device than that controlling the UV lamps 522, so that operation of the UV lamps 524 may be separately controlled. Additionally, an ozone detector (not shown) may be provided on the ADHVAC 100 and/or in the PIE to monitor ozone levels in the air, as discussed in '041 application and the '1041 publication, which are incorporated by reference herein. A timer (not shown) may also be provided in the ADHVAC to set the amount of time the ozone generators operate. A processor, such as the microprocessor 215, may also control these operations.

Decontamination of the ADHVAC 100 itself after operation may be provided by generating ozone O from ozone generators while operating the blower 104 to distribute the ozone throughout the ADHVAC. The ADHVAC 100 would then become flooded with ozone, decontaminating components of the unit along the air path, as is also discussed in the '041 application and the '104 publication, which are incorporated by reference herein.

Other applications for the ADHVAC 100, IHVAC 400*a*, 400*b*, and the PICS 200 in accordance with the present invention include command and control centers and facilities to prepare food and drugs at a disaster site, for example.

While particular temperature and extreme temperature ranges are discussed above, the ADHVACs and IHVACs of the present invention may operate in other temperature ranges, including more extreme temperature ranges and narrower temperature ranges.

The embodiments described above are examples of implementations of the present invention. One of skill in the art will recognize that changes may be made to the described embodiments without going beyond the spirit and scope of the invention, which is defined in the following claims.

What is claimed is:

1. An integrated air processing device, comprising:
a housing defining an air inlet, an air outlet, and a pathway from the inlet to the outlet;
an air decontamination section along the pathway;
an air conditioning section along the pathway;
a heating section along the pathway;
a blower along the pathway, to drive air from the inlet to the outlet, along the pathway;
wherein at least one of the air conditioning section and the heating section modifies speed of air flow along a first portion of the pathway within the at least one section, in relation to speed of air flow along a portion of the pathway upstream of the first portion; and
wherein the heating section and the air conditioning section are operable for providing heating and cooling, respectively, over a predetermined temperature range.

2. The air processing device of claim 1, wherein:
the blower is downstream of the air decontamination section; and
the blower is upstream of the air conditioning section and the heating section.

3. The air processing device of claim 1, wherein:
the housing further defines an inlet vent upstream of the blower and separate from the air inlet, to allow for the entry of air to the pathway.

4. The air processing device of claim 3, wherein:
the housing further defines an outlet vent downstream of the blower and separate from the air outlet, to allow for the exit of air from the pathway.

5. The air processing device of claim 1, wherein:
the housing further defines an outlet vent downstream of the blower and separate from the air outlet, to allow for the exit of air from the pathway.

6. The air processing device of claim 1, wherein the air conditioning section comprises:
an evaporator along the pathway, the evaporator having an upper portion and a lower portion; wherein:
the housing defines a plurality of passages along the air pathway, the passages having an outlet facing the evaporator; and
the passages are configured so that more air is directed toward the lower portion of the evaporator than the upper portion of the evaporator.

7. The air processing device of claim 1, wherein the air conditioning section comprises:
an evaporator along the pathway; and
a damper movably supported with respect to the pathway, upstream of the evaporator, so that the damper may be selectively moved across the pathway to vary air flow along the pathway, to the evaporator.

8. The air processing device of claim 1, wherein the air conditioning section comprises:
an evaporator transverse to the pathway.

9. The air processing device of claim 1, wherein the air conditioning section includes an evaporator, the device further comprising:
means for varying airflow to the evaporator, when the air conditioning section is activated.

10. The air processing device of claim 9, wherein:
the evaporator has a downstream face through which air exits the evaporator, the downstream face having a surface area;
the outlet has an entrance defining a first area less than the surface area; and
the heating section comprises at least one heating element occupying a second area about the same size as the first area.

11. The air processing device of claim 10, wherein:
the outlet is circular and has a first diameter; and
the heating elements comprise heating coils wound in a circular shape having a second diameter about equal to the first diameter.

12. The air processing device of claim 1, wherein:
the air conditioning section includes an evaporator;
the evaporator has an downstream face through which air exits the evaporator, the downstream face having a surface area;
the outlet has an entrance defining a first area less than the surface area; and
the heating section comprises at least one heating element occupying a second area about the same size as the first area.

13. The air processing device of claim 1, wherein:
the air decontamination section comprises:
a V-bank filter defining at least one upstream facing V-shaped chamber and at least one downstream facing V-shaped chamber;
an ultraviolet lamp at least partially within each V-shaped chamber; and
a reflector facing each V-shaped chamber, to direct ultraviolet radiation emitted in a direction away from a respective each V-shaped chamber, towards the respective V-shaped chamber, during operation.

14. The air processing device of claim 1, wherein:
the air conditioning section is operable as a heat pump.

15. The air processing device of claim 1, further comprising:
a processor coupled to the device, wherein the processor is configured to:
at least one of monitor operation of the device and control operation of the device.

16. The air processing device of claim 1, wherein:
the blower has at least one first speed when the air conditioning section is on and at least one second speed when the air conditioning section is off, the second speed being greater than the first speed.

17. An integrated air processing device, comprising:
a housing defining an air inlet, an air outlet, and a pathway from the inlet to the outlet;
an air conditioning section along the pathway;
a heating section along the pathway;
wherein at least one of the air conditioning section and the heating section modifies speed of air flow along a first portion of the pathway within the at least one section, in relation to speed of air flow along a portion of the pathway upstream of the first portion; and
wherein the heating section and the air conditioning section are operable for providing heating and cooling, respectively, over a predetermined temperature range.

18. The air processing device of claim 17, wherein:
the air conditioning section comprises an evaporator having an upper portion and a lower portion; and
the housing is configured to differentially direct air toward the evaporator, to decrease air flow through the evaporator, when the air conditioning section is activated.

19. The air processing device of claim 18, wherein:
the housing is configured to direct more air onto the lower portion of the evaporator than onto the upper portion, during operation.

20. The air processing device of claim 19, comprising;
a plurality of channels along the pathway, to direct more air onto the lower portion of the evaporator than onto the upper portion.

21. The air processing device of claim 17, wherein the air conditioning section comprises:
an evaporator along the pathway; and
a damper movably supported with respect to the pathway, upstream of the evaporator, so that the damper may be selectively moved across the pathway to vary airflow along the pathway, to the evaporator.

22. The air processing device of claim 17, wherein the air conditioning section comprises:
an evaporator transverse to the pathway.

23. The air processing device of claim 17, wherein:
the air conditioning section includes an evaporator;
the evaporator has a downstream face through which air exits the evaporator, the downstream face having a surface area;

the outlet has an entrance defining a first area less than the surface area; and the heating section comprises heating elements occupying a second area about the same size as the first area.

24. The air processing device of claim 23, wherein:
the outlet has a circular shape having a first diameter; and
the heating elements comprise at least one heating coil wound in a circular shape having a second diameter about equal to the first diameter.

25. The air processing device of claim 17, wherein:
the housing further defines an inlet vent separate from the air inlet, to allow for the entry of air to the pathway.

26. The air processing device of claim 25, wherein:
the housing further defines an outlet vent separate from the air outlet, to allow for the exit of air from the pathway.

27. The air processing device of claim 17, wherein: the housing further defines an outlet vent separate from the air outlet, to allow for the exit of air from the pathway.

28. The air processing device of claim 17, further comprising:
an air decontamination section along the pathway.

29. The air processing device of claim 17, further comprising:
a blower along the pathway to drive air from the inlet to the outlet, along the pathway.

30. The air processing device of claim 18, comprising:
a blower along the pathway to drive air from the inlet to the outlet, along the pathway;
a first channel to direct air towards the lower portion of the evaporator;
at least one second channel to direct air towards the upper portion of the evaporator; wherein:
the blower is positioned to drive more air into the first channel than into the second channel.

31. The air processing device of claim 30, wherein:
about half of the air is directed into the first channel and about half of the air is directed into the at least one second channel.

32. The air processing device of claim 31, wherein:
the lower portion of the evaporator comprises a lower third of the evaporator; and
the upper portion of the evaporator comprises an upper two thirds of the evaporator.

33. The air processing device of claim 29, wherein:
the blower has at least one first speed when the air conditioning section is on and at least one second speed when the air conditioning section is off, the second speed being greater than the first speed.

34. A portable isolation system, comprising:
a portable containment enclosure defining an interior to house subjects; and
an integrated air processing device to provide air conditioning and heating, the air processing device (i) defining an air inlet, an air outlet, and a pathway from the inlet to the outlet and (ii) being coupled to the enclosure to process air within the enclosure;
wherein the air processing device modifies speed of air flow along a first portion of the pathway, in relation to speed of air flow along a portion of the pathway upstream of the first portion; and
wherein the air processing device is operable for providing heating and cooling over a predetermined temperature range.

35. The portable isolation system of claim 34, wherein:
the integrated air processing device comprises:
a housing defining the air inlet, the air outlet, and the pathway;
an air conditioning section along the pathway; and
a heating section along the pathway.

36. The portable isolation system of claim 35, wherein:
the air conditioning section comprises an evaporator having an upper portion and a lower portion; and
the housing is configured to direct more air onto the lower portion of the evaporator than onto the upper portion of the evaporator.

37. The portable isolation system of claim 35, wherein the air conditioning section comprises:
an evaporator along the pathway; and
a damper movably supported with respect to the pathway, upstream of the evaporator, so that the damper may be selectively moved across the pathway to vary airflow along the pathway, to the evaporator.

38. The portable isolation system of claim 35, wherein the air conditioning section comprises:
an evaporator transverse to the pathway.

39. The portable isolation system of claim 35, wherein:
the inlet is coupled to the interior of the portable containment enclosure to receive air from the interior of the enclosure;
the outlet is coupled to the interior of the portable containment enclosure to provide processed air to the interior of the enclosure; and
the housing further defines:
an inlet vent separate from the air inlet, through which air external to the portable containment enclosure is drawn into the air processing device, whereby opening the inlet vent creates a positive pressure within the portable containment enclosure, during operation.

40. The portable isolation system of claim 39, further comprising:
a slidable damper to open and close the inlet vent;
wherein the vent is positioned adjacent to the inlet of the air processing device whereby movement of the damper to open the vent moves the damper to partially close the inlet.

41. The portable isolation system of claim 39, wherein:
the housing further defines an outlet vent separate from the outlet, through which air exits the pathway, exterior to the portable containment enclosure whereby opening the outlet vent during operation creates a negative pressure within the containment enclosure, during operation.

42. The portable isolation system of claim 35, wherein the housing further defines:
an air outlet vent along the pathway, through which air exits the pathway exterior to the portable containment enclosure during operation, wherein opening of the vent creates a negative pressure within the containment enclosure.

43. The portable isolation system of claim 34, further comprising:
at least one second portable containment enclosure coupled to the first enclosure, wherein personnel may pass between the enclosures; and
at least one respective second integrated air processing device coupled to the second enclosure, to provide at least one of air conditioning and heating to the at least one second portable containment enclosure, during operation.

44. The portable isolation system of claim 43, wherein:
the first air processing device creates one of a positive pressure and a negative pressure in the first enclosure during operation.

45. The portable isolation system of claim 44, wherein:
the at least one second air processing device creates the other of the positive pressure and the negative pressure in the at least one second enclosure.

46. The portable isolation system of claim 43, further comprising:
a chamber between the first portable containment enclosure and the at least one second portable containment enclosure.

47. The portable isolation system of claim 43, wherein:
the first integrated air processing device and the at least one second integrated air processing device further provide air decontamination of the air in the first containment enclosure and the at least one second enclosure.

48. The portable isolation system of claim 34, wherein:
the portable containment enclosure comprises a tent.

49. The portable isolation system of claim 34, further comprising:
a processor coupled to at least one of the integrated air processing device and the portable containment enclosure, wherein the processor is configured to:
at least one of monitor and control the operation of the system.

50. The portable isolation system of claim 34, further comprising:
a high efficiency gas absorber device coupled between the integrated air processing device and the portable isolation enclosure.

51. The portable isolation system of claim 35, wherein the integrated air processing device further comprises:
an air decontamination section.

52. The portable isolation system of claim 35, wherein:
the air conditioning section comprises an evaporator having a downstream side having a surface area;
the outlet has an entrance defining a first area less than the surface area; and
the heating section comprises at least one heating element occupying a second area about the same size as the first area.

53. The portable isolation system claim 35, further comprising:
a blower along the pathway, to drive air from the inlet to the outlet, along the pathway.

54. The portable isolation system of claim 53, wherein:
the blower has at least one first speed when the air conditioning section is on and at least one second speed when the air conditioning section is off, the second speed being greater than the first speed.

55. A method of processing air by a device, the device comprising an air conditioning section and a heating section, wherein an air pathway extends from an inlet of the device, through the air conditioning and heating sections, to an outlet of the device, the method comprising:
receiving air through the inlet to the device;
cooling a first air flow passing through the air conditioning section, when the air conditioning section is on;
heating a second air flow passing through the heating section, when the heating section is on, wherein the second air flow is greater than the first air flow; and
driving air out of the device, through the outlet.

56. The method of claim 55, comprising:
driving air along the pathway, from the inlet, through the air conditioning section, then through the heating section, and then out of the device.

57. The method of claim 56, further comprising:
decreasing the air flow through at least the air conditioning section from the second air flow to the first air flow, when the air conditioning section is on.

58. The method of claim 55, comprising:
processing air received from the portable containment enclosure; and
returning processed air to the portable containment enclosure.

59. The method of claim 58, further comprising:
creating at least one of a positive pressure and a negative pressure in the enclosure, by the device.

60. The method of claim 59, further comprising:
creating one of a positive pressure and negative pressure in the enclosure, by the device; and then
creating the other of the positive pressure and the negative pressure in the enclosure, by the device.

61. The method of claim 55, further comprising:
converting the air conditioning section into a heat pump; and
heating the second air flow, at least in part, by the heat pump.

62. The method of claim 55, wherein the device further comprises an air decontamination section, the method further comprising:
decontaminating the air.

63. A portable isolation system, comprising:
a portable containment enclosure;
an air decontamination device (i) defining an air inlet, an air outlet, and a pathway from the inlet to the outlet, and (ii) coupled to the enclosure to decontaminate, heat and cool air within the enclosure;
wherein the air decontamination device modifies speed of air flow along a first portion of the pathway, in relation to speed of air flow along a portion of the pathway upstream of the first portion; and
wherein the air decontamination device is operable for providing heating and cooling over a predetermined temperature range.

64. The air processing device of claim 1, wherein the predetermined temperature range is at least one of about (i) 0° F. to 100° F., and (ii) −20° F. to 120° F.

* * * * *